(12) United States Patent
Pillai et al.

(10) Patent No.: US 10,005,884 B2
(45) Date of Patent: Jun. 26, 2018

(54) METHODS FOR PURIFYING 2-ARYL-3,3-BIS(HYDROXYARYL) PHTHALIMIDINES

(71) Applicant: SABIC GLOBAL TECHNOLOGIES B.V., Bergen op Zoom (NL)

(72) Inventors: Anup Krishnnan Appukuttan Pillai, Karnataka (IN); Shivakumar Konda, Karnataka (JP); Gaurav Mediratta, Karnataka (JP); Venkata Rama Narayanan Ganapathy Bhotla, Karnataka (IN); Salkod Parameshwar Mallika, Karnataka (IN); Pradeep Jeevaji Nadkarni, Karnataka (IN)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days. days.

(21) Appl. No.: 15/302,510

(22) PCT Filed: Apr. 22, 2015

(86) PCT No.: PCT/IB2015/052922
§ 371 (c)(1),
(2) Date: Oct. 7, 2016

(87) PCT Pub. No.: WO2015/162564
PCT Pub. Date: Oct. 29, 2015

(65) Prior Publication Data
US 2017/0029562 A1 Feb. 2, 2017

(30) Foreign Application Priority Data
Apr. 23, 2014 (IN) .......................... 1100/DEL/2014

(51) Int. Cl.
*C08G 63/02* (2006.01)
*C08G 64/12* (2006.01)
*C07D 209/46* (2006.01)

(52) U.S. Cl.
CPC ........... *C08G 64/12* (2013.01); *C07D 209/46* (2013.01)

(58) Field of Classification Search
CPC .................................................... C08G 64/12

USPC ......................................... 528/196, 198, 208
See application file for complete search history.

(56) References Cited

U.S. PATENT DOCUMENTS

| 7,790,832 B2 | 9/2010 | Ganesan et al. |
| 7,884,220 B2 | 2/2011 | Xu et al. |
| 2012/0309926 A1 | 12/2012 | Bhotla et al. |

FOREIGN PATENT DOCUMENTS

| EP | 2367792 | * 10/1977 | ........... C07D 209/46 |
| EP | 1763512 B1 | 9/2010 | |
| WO | 2007070528 A1 | 6/2007 | |
| WO | 2010067330 A1 | 6/2010 | |

OTHER PUBLICATIONS

EP 2367792 Methods for Producing and Purifying 2-Aryl-3,3-Bis (4-Hydroxyaryl) Phthalimidine Derivatives; PUBN-Date: Sep. 28, 2011—abstract-.*
International Search Report; International Application No. PCT/IB2015/052922; International Filing Date Apr. 22, 2015; dated Sep. 2, 2015; 5 pages.
Written Opinion of the International Searching Authority; International Application No. PCT/IB2015/052922; International Filing Date Apr. 22, 2015; dated Sep. 2, 2015; 5 pages.

* cited by examiner

*Primary Examiner* — Terressa M Boykin
(74) *Attorney, Agent, or Firm* — Cantor Colburn LLP

(57) ABSTRACT

Methods for synthesizing and purifying 2-aryl-3,3-bis(4-hydroxyaryl)phthalimidine compounds are provided. The method includes heating a reaction mixture including a phenolphthalein, a primary aryl amine, and an acid catalyst to form a phthalimidine; precipitating the phthalimidine from the reaction mixture to provide a crude phthalimidine; providing a solution including the crude phthalimidine, an additive, and at least one solvent; contacting the solution with one or more purification agents to provide a treated solution; precipitating and recovering a phthalimidine adduct from the treated solution; and recovering a purified phthalimidine compound from the adduct.

20 Claims, No Drawings

METHODS FOR PURIFYING 2-ARYL-3,3-BIS(HYDROXYARYL) PHTHALIMIDINES

CROSS REFERENCE TO RELATED APPLICATIONS

This application is a 371 of International Application No. PCT/M2015/052922, filed Apr. 22, 2015, which claims priority to Indian Patent Application No. 1100/DEL/2014, filed Apr. 23, 2014, which are incorporated herein by reference in their entirety.

TECHNICAL FIELD

The present disclosure generally relates to 2-aryl-3,3-bis (4-hydroxyaryl)phthalimidine compounds, methods for producing and purifying the compounds, and polymers derived from the compounds.

BACKGROUND

Phenolphthalein derivatives have been used as aromatic dihydroxy compound monomers to prepare polycarbonate resins as well as polyarylate resins. Phenolphthalein derivatives can be difficult to make and isolate with sufficient purity for use in polymer synthesis. Currently available methods to make and isolate phenolphthalein derivatives are lengthy and resource intensive. Accordingly, there remains an unmet need for methods of making and isolating phenolphthalein derivatives suitable for use in polymer synthesis.

DETAILED DESCRIPTION

The present disclosure relates to methods of producing and purifying phenolphthalein derivatives, in particular 2-aryl-3,3-bis(4-hydroxyaryl)phthalimidine compounds. The 2-aryl-3,3-bis(4-hydroxyaryl)phthalimidine compounds produced in accordance with these methods can be used in the manufacture of polycarbonates and other polymers having improved properties, such as lower visual coloration and a higher weight average molecular weight. The 2-aryl-3,3-bis(4-hydroxyaryl)phthalimidine compounds can further have higher degradation temperatures, and/or reduced color upon heating.

The disclosed methods provide several advantages over current processes. The methods provide for solvent recovery and recyling, thereby minimizing solvent requirements for production of the target compound(s). The methods provide for use of purification agents that can be recycled and regenerated for use in several cycles of compound production and purification. The methods provide for reduced cycle time to produce and purify the target phthalimidine compound(s). The methods provide for minimal carbon use, and use of low cost carbon materials for purification. The methods provide for minimal effluent treatment with minimal or no salt disposal. The methods provide for improved yield over current processes (e.g., 93% to 95% yield; versus 88% to 90% yield). The methods provide for processes that can run continuously to produce the target phthalimidine compound(s).

1. Definition of Terms

All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "AHP" as used herein refers to 2-aryl-3,3-bis (hydroxyaryl)phthalimidine. The term "AHAP" as used herein refers to 2-aryl-3-(hydroxyaryl)-3-(aminoaryl)phthalimidine. The term "PP" as used herein refers to phenolphthalein.

"Copolymer" as used herein may mean a polymer derived from two or more structural unit or monomeric species, as opposed to a homopolymer, which is derived from only one structural unit or monomer.

"Halo" as used herein may be a substituent to which the prefix is attached is substituted with one or more independently selected halogen radicals. For example, "$C_1$-$C_6$ haloalkyl" means a $C_1$-$C_6$ alkyl substituent wherein one or more hydrogen atoms are replaced with independently selected halogen radicals. Non-limiting examples of $C_1$-$C_6$ haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

"Halogen" or "halogen atom" as used herein may mean a fluorine, chlorine, bromine or iodine atom.

"Hydrocarbyl" as used herein refers to a monovalent moiety formed by removing a hydrogen atom from a hydrocarbon. Representative hydrocarbyls are alkyl groups having 1 to 25 carbon atoms, such as, for example, methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; arylalkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Purified Phthalimidine Compounds

Disclosed are purified 2-aryl-3,3-bis(4-hydroxyaryl) phthalimidine compounds of formula (I),

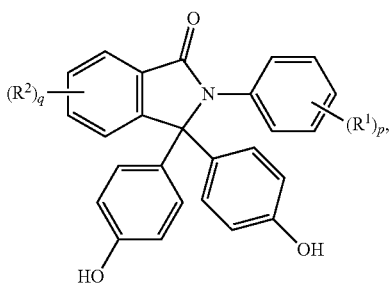

(I)

wherein R¹, at each occurrence, is selected from $C_1$-$C_{25}$ hydrocarbyl; R₂, at each occurrence, is selected from $C_1$-$C_{25}$ hydrocarbyl and halogen; p is 0, 1, 2, 3, 4, or 5; and q is 0, 1, 2, 3, or 4.

In certain embodiments, p is 0 and q is 0, wherein the compound of formula (I) is 2-phenyl-3,3-bis(4-hydroxyphenyl)phthalimidine ("PPPBP"),

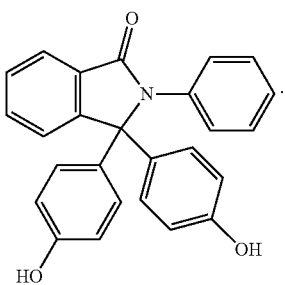

(PPPBP)

The purified compound of formula (I), such as PPPBP, can have a purity of 99.80% or greater, 99.85% or greater, 99.90% or greater, 99.95% or greater. The purified compound of formula (I) can have an aminophenol impurity content of 200 ppm or less, 150 ppm or less, 100 ppm or less, 90 ppm or less, 80 ppm or less, 70 ppm or less, 60 ppm or less, 50 ppm or less, 40 ppm or less, 30 ppm or less, 20 ppm or less, or 10 ppm or less. The amino phenol impurity may be 2-phenyl-3-(4-aminophenyl)-3-(4-hydroxyphenyl) phthalimidine. The purified compound of formula (I) can have a phenolphthalein impurity content of 1,000 ppm or less, 750 ppm or less, 500 ppm or less, 400 ppm or less, 300 ppm or less, 200 ppm or less, 100 ppm or less, 50 ppm or less. The purified compound of formula (I) can have a metal impurity content of 3 ppm or less, 2 ppm or less, 1 ppm or less, 500 ppb or less, 400 ppb or less, 300 ppb or less, 200 ppb or less, or 100 ppb or less. The metal impurities may be iron, calcium, zinc, aluminum, or a combination thereof. The purified compound of formula (I) can have a urea impurity content of 20 ppm or less, 15 ppm or less, 10 ppm or less, or 5 ppm or less. The purified compound of formula (I) can have a methanol solvent content of 100 ppm or less, 75 ppm or less, 50 ppm or less, 40 ppm or less, 30 ppm or less, 20 ppm or less, or 10 ppm or less. The purified compound of formula (I) can have an unknown impurities content of 0.1 wt % or less. The purified compound of formula (I) can have a color APHA value of 40 or less, 35 or less, 30 or less, 25 or less, 20 or less, 19 or less, 18 or less, 17 or less, 16 or less, or 15 or less, as measured using test method ASTM D1209.

The purified compound of formula (I), such as PPPBP, can be produced by the disclosed methods with a yield of 70% or greater, 80% or greater, 85% or greater, 86% or greater, 87% or greater, 88% or greater, 89% or greater, 90% or greater, 91% or greater, 92% or greater, 93% or greater, 94% or greater, 95% or greater.

Compounds of formula (I), such as PPPBP, can be prepared by the reaction of a phenolphthalein material and a hydrocarbyl amine. In certain embodiments, compounds of formula (I) can be prepared by heating a reaction mixture including a phenolphthalein of formula (II), a primary aryl amine of formula (III), and an acid catalyst,

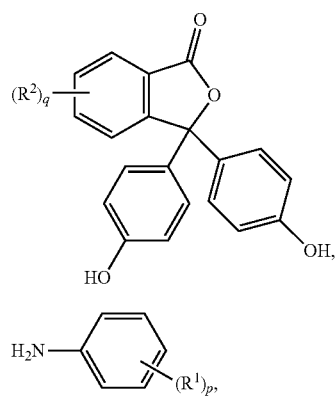

(II)

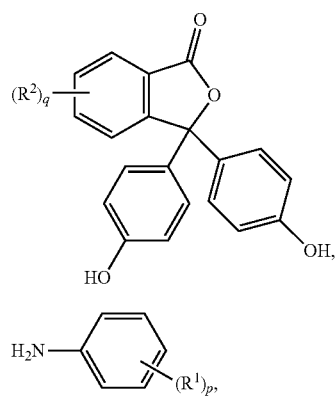

(III)

wherein R¹, at each occurrence, is selected from $C_1$-$C_{25}$ hydrocarbyl; R₂, at each occurrence, is selected from $C_1$-$C_{25}$ hydrocarbyl and halogen; p is 0, 1, 2, 3, 4, or 5; and q is 0, 1, 2, 3, or 4.

An acid catalyst is used to facilitate formation of the phthalimidine product. Suitable acid catalysts include, but are not limited to, mineral acids such as hydrochloric acid (HCl), sulfuric acid, nitric acid, and phosphoric acid; weak inorganic acids such as boric acid, organic sulfonic acids such as methanesulfonic acid, Lewis acids such as stannic chloride, ferric chloride, aluminum trichloride, and zinc dichloride; sulfated zirconia; or combinations of two or more of the foregoing acid catalysts. In certain embodiments, the acid catalyst is hydrochloric acid, such as 35% concentrated hydrochloric acid.

Suitable acid catalysts also include amine salts of the above mineral acids. Examples of suitable amines include primary, secondary, and tertiary amines having any combination of aliphatic and aromatic groups bonded to the amine nitrogen. Suitable examples of amine salt catalysts include primary, secondary, and tertiary amine hydrochlorides. Hydrochloride salts of the primary aromatic amines of formula (III) are especially useful since the amines of formula (III) also serve as the starting material for preparing the phthalimidines of formula (I).

The acid catalyst can be introduced as a pre-formed salt into the reactor. Alternatively, the catalyst can be generated in the reactor by first charging an amine of formula (III) into the reactor and then adding 0.1 to 1 part by weight based on the total weight of the amine of an appropriate mineral acid to the reactor. In one embodiment, 0.1 to 0.3 part by weight of hydrogen chloride gas based on the total weight of the amine is introduced into a reactor charged with the amine to form an appropriate amount of the amine hydrochloride catalyst. More hydrochloric acid or more hydrogen chloride gas can also be used, but is generally not required. A solvent can optionally be employed to form the amine hydrochloride. The solvent can then be removed (if necessary), and the amine of formula (III) can be added, followed by addition of phenolphthalein (II).

The reaction of phenolphthalein (II) with the amine (III) proceeds by a condensation reaction to form the desired phthalimidine product (I). An excess of the amine over the phenolphthalein may be used to keep the reaction proceeding in the forward direction. Likewise, a higher reaction temperature with or without water by-product removal can facilitate product formation. However, in order to enhance the selectivity of 2-hydrocarbyl-3,3-bis(4-hydroxyaryl) phthalimidine (I), and suppress the formation of undesired by-product, for example, 2-hydrocarbyl-3,3-{(2-hydroxyaryl)(4-hydroxyaryl)}phthalimidine or 2-hydrocarbyl-3,3-{(4-hydroxyaryl)(4-aminoaryl)}phthalimidine, it is useful to control the temperature of the reaction mixture and the rate of water removal. The temperature of the reaction mixture can be controlled such that the crude product is greater than or equal to 97 weight (wt %) percent, or more specifically, greater than or equal to 99 wt % percent, of 2-hydrocarbyl-3,3-bis(4-hydroxyaryl)phthalimidine. The chemical structures of the (2-hydroxyaryl)(4-hydroxyaryl)phthalimidine and (4-hydroxyaryl)(4-aminoaryl)phthalimidine by-products are shown in formulas (IV) and (V), respectively:

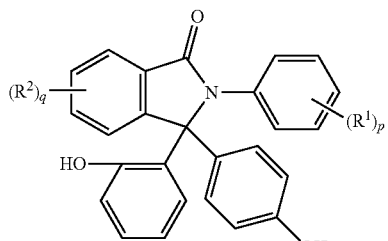

(IV)

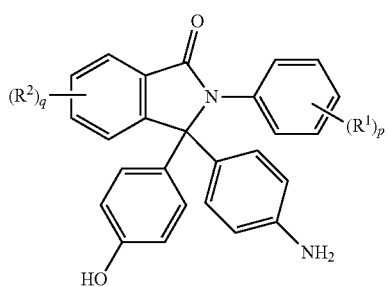

(V)

wherein $R^1$, at each occurrence, is selected from $C_1$-$C_{25}$ hydrocarbyl; $R_2$, at each occurrence, is selected from $C_1$-$C_{25}$ hydrocarbyl and halogen; p is 0, 1, 2, 3, 4, or 5; and q is 0, 1, 2, 3, or 4. In certain embodiments, p and q are each 0 in each of formulas (IV) and (V).

In certain embodiments, the reaction temperature is controlled such that the water by-product (calculated based on the moles of the phenolphthalein (II) which is used as the limiting reagent) distills over a period of 8 hours to 50 hours, or more specifically, 12 hours to 24 hours. If the reaction mixture is heated such that the amount of water by-product distills within 6 hours, the phthalimidine product of formula (I) can have a relatively greater amount of the (4-hydroxyaryl)(4-aminoaryl)phthalimidine impurity shown in formula (V). Therefore, although a higher reaction temperature ensures a quicker consumption of the phenolphthalein (II) material, it can lead to formation of a higher amount of the impurity of formula (V) and other impurities can also increase with an increase in temperature and time. If the reaction temperature is not sufficiently high, a relatively large amount of the phenolphthalein material remains unreacted, thereby leading to an inferior product, e.g., forms a less stable polymer during polymerization and subsequent melt mixing, (phenolphthalein can be incorporated into the polycarbonate like 2-hydrocarbyl-3,3-bis(4-hydroxyaryl) phthalimidine) and the like.

Thus, in certain embodiments, the reaction mixture is heated to a temperature of 140° C. to 180° C. to remove water by-product and form the desired 2-hydrocarbyl-3,3-bis(4-hydroxyaryl)phthalimidine product. In certain embodiments, the reaction mixture is heated to a temperature of 140° C. to 160° C. for 20 hours to 50 hours. In certain embodiments, the reaction mixture is heated to a temperature of 140° C. to 145° C. for 45 hours. In certain embodiments, the reaction mixture is heated to a temperature of 152° C. to 157° C. for 12 hours to 24 hours. In certain embodiments, the reaction mixture is heated to a temperature of 153° C. to 155° C. for 12 hours to 24 hours. In certain embodiments, the reaction mixture is heated to a temperature of 153° C. to 155° C. for 22 hours.

By way of example, phenolphthalein (q is 0 in formula (II)) can be reacted with aniline (p is 0 in formula (III)) in the presence of hydrochloric acid as a catalyst to form 2-phenyl-3,3-bis(4-hydroxyphenyl)phthalimidine (referred to herein as "PPPBP").

Isolation of the desired phenolphthalein derivative of formula (I) from the reaction mixture includes quenching the reaction mixture and treating the quenched mixture to obtain a crude phthalimidine. In certain embodiments, the crude phthalimidine product can be isolated from the reaction mixture by cooling the reaction mixture; quenching the reaction mixture with an acid (e.g., aqueous hydrochloric acid, such as 10% aqueous HCl or 35% conc. HCl); filtering the precipitate; and washing the precipitate to provide the crude phthalimidine.

Prior to adding an acid to quench the reaction mixture, the reaction mixture can be cooled to, for example, 100° C. to 120° C. The reaction mixture can be cooled to 100° C., 105° C., 110° C., 115° C., 120° C., or 125° C.

The reaction mixture can be quenched with an acid such as an aqueous mineral acid which precipitates a solid comprising 2-hydrocarbyl-3,3-bis(4-hydroxyaryl)phthalimidine. An exemplary aqueous mineral acid is aqueous hydrochloric acid. Other suitable acids include, but are not limited to, sulfuric acid, boric acid, phosphoric acid, acetic acid, nitric acid, or combinations of two or more of the foregoing mineral acids. The quenched reaction mixture can be stirred over a time period of 1 hour, for example. The quenched reaction may thereafter be further cooled to, for example, 10° C. to 25° C.

The crude phthalimidine precipitate may be part of a slurry. The crude phthalimidine precipitate can be isolated from the slurry. Suitable isolation methods include filtration, centrifugation and combinations thereof. In certain embodiments, the slurry is filtered to obtain the precipitate, the precipitate is washed (e.g., with deionized water), and then the precipitate is dried via centrifugation. The filtration can be conducted either at reduced temperature (e.g., 10° C.), at room temperature (25° C.), or at an elevated temperature (e.g., 25° C. to 90° C.).

The crude phthalimidine can include 1,000 ppm to 3,000 ppm, 1,200 ppm to 2,500 ppm, 1,200 ppm to 1,700 ppm, or 1,200 ppm to 1,500 ppm of an amino phenol impurity (e.g., aminophenol of formula (V)). The crude phthalimidine can include 0.2 wt % to 0.4 wt % of an aminophenol impurity (e.g., aminophenol of formula (V)). The crude phthalimidine can include 0.5 wt % to 3 wt %, or 1 wt % to 2 wt % of residual phenolphthalein of formula (II). The crude phthalimidine can have a moisture level of 20 wt % to 30 wt % with respect to the crude phthalimidine product. The yield of the crude phthalimidine can be 99% (based on dry weight). The purity of the crude phthalimidine can be 98%.

Phthalimidine compounds can form insoluble adducts (e.g., phthalimidine-methanol adducts) during purification processes. One or more additives can be advantageously used to delay formation of phthalimidine adduct(s) until such time as it is desirable to precipitate a phthalimidine adduct. In certain embodiments, the additive can be toluene. In certain embodiments, the additive can be urea, having formula (VI):

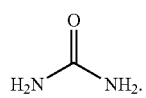

(VI)

In certain embodiments, the crude phthalimidine can be provided into (e.g., dissolved in) a solution including the crude phthalimidine, the additive (e.g., urea), and at least one solvent. The solution solution can be at a temperature of 55° C. to 60° C., for example. The solution can be stirred for a period of 30 minutes to 1 hour, for example.

Optionally, the crude phthalimidine can be washed prior to dissolving in the solution. For example, the crude phthalimidine can be washed with a methanol:water mixture (e.g., a 90:10 methanol:water mixture) at a temperature of 10° C., and thereafter dried (e.g., suction dried in a Buchner funnel).

The at least one solvent can be an organic solvent. The at least one solvent can be an organic hydroxy compound, an organic ketone compound, an organic amide compound, an organic sulfoxide compound, an organic nitrile compound, an organic amine compound, an organic aromatic compound, or a combination thereof. The at least one solvent can be methanol, toluene, or a combination thereof. The at least one solvent can be methanol. The at least one solvent can be methanol and toluene in a ratio of 2-5:1 by volume. The at least one solvent can be methanol and toluene in a ratio of 3-4:1 by volume. The at least one solvent can be methanol and toluene in a ratio of 3.5:1 by volume.

The volumes of the at least one solvent to the crude phthalimidine can be 7-27:1. The volumes of the at least one solvent to the crude phthalimidine can be 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, or 27:1.

The additive (e.g., urea additive) may be present in 5 wt % to 10 wt % based on wt % of the crude phthalimidine. The additive (e.g., urea additive) may be present in 5 wt %, 6 wt %, 7 wt %, 8 wt %, 9 wt %, or 10 wt % based on wt % of the crude phthalimidine.

The crude phthalimidine in solution with the additive can be treated with one or more purification agents. For example, the solution of crude phthalimidine can be treated with a commercial grade activated carbon, an ion exchange resin, or a combination thereof. In certain embodiments, the solution is not treated with an activated carbon. The solution can optionally be treated with other purification agents. The purification agents can be removed from the solution by filtration. In certain embodiments, the crude phthalimidine solution is at a temperature of 55° C. to 60° C. when undergoing treatment with one or more of the purification agents.

The solution can be treated with purification agents concurrently or consecutively, for example Each treatment may be for a period of 1 hour to 2 hours, for example. In certain embodiments, the solution is treated with commercial grade activated charcoal for one hour at a temperature of 55° C. to 60° C.; the solution is filtered to remove the charcoal; and the solution is treated with an ion exchange resin for two hours at a temperature of 55° C. to 60° C.

The loading of the purification agents can be any selected weight percent relative to the crude phthalimidine. For example, the loading of the one or more purification agents can from 5 wt % to 200 wt %, 5 wt % to 75 wt %, or 5 wt % to 50 wt %, based on wt % of the crude phthalimidine. In certain embodiments, the loading of the one or more purification agents into the solution is 5, 10 wt %, 15 wt %, 20 wt %, 25 wt %, 30 wt %, 35 wt %, 40 wt %, 45 wt %, 50 wt %, 55 wt %, 60 wt %, 65 wt %, or 70 wt % or greater, based on wt % of the crude phthalimidine.

The activated carbon can be a commercially available activated carbon. The activated carbon may be a low cost activated charcoal. Activated carbon purification agents include, but are not limited to, the NORIT series of activated carbon available from Norit Corporation, and those activated carbons commercially available from E. Merck Company.

The activated carbon may be activated carbon fibers. The activated carbon fibers can be packed into a column for ease of use. Activated carbon fibers may be formed from cellulose and acrylic precursors. Activated carbon fibers are usually provided in the form of a sheet. This sheet may be rolled up and packed into the column. Alternately, the sheet may be cut into chips and then packed into the column. The chips may have any shape; in certain embodiments, the chips are cut into circles and then stacked on top of each other into the column. In certain embodiments, two types of circular chips having two diameters are alternately stacked into the column. These forms allow the column to be packed with near 100% efficiency.

After treatment with activated carbon, the resulting mixture can be filtered or removed by centrifugation, to provide a solution that is then treated with an ion exchange resin, for example.

The ion exchange resin can be any organic polymer comprising at least one Bronsted acidic functional group. Bronsted acidic functional groups are exemplified by sulfonic acid groups, carboxylic acid groups, phosphorus-based acidic groups comprising one or more P—OH bonds, and the like. Non-limiting examples of acidic organic polymers include poly(styrenesulfonic acid), poly(vinylsulfonic acid), poly(vinylphosphonic acid), and the like. Homopolymers and copolymers of these acidic organic polymers can be used. In some cases, the acidic organic polymer can be used as a solution in a suitable solvent, such as water. Generally, however, it is preferable to use the acidic organic polymer in an insoluble form for removing impurities (e.g., aminophenol and phenophthalein). Cross-linked acidic organic polymers are generally insoluble and can be used. Suitable insoluble acidic organic polymers include the acidic ion exchange resin class of materials. These materials generally comprise a sulfonated product of a polystyrene that is cross-linked with divinylbenzene. Thus, any of the sulfonated polystyrene resins comprising up to 20 weight percent of divinylbenzene, relative to an overall weight of the resin can be used. More specifically, the acidic ion exchange resin is a sulfonated polystyrene resin crosslinked with up to 4 weight percent of divinylbenzene relative to an overall weight of the resin.

In certain embodiments, the ion exchange resin is an acidic ion exchange resin having an acid milliequivalents/gram of 4.8 to 5.0, and optionally 2% crosslinking.

The ion exchange resin can be in the form of insoluble beads, which can be filtered out of solution after use. The ion exchange resin can be provided in a packed column or bed, through which the solution of crude phthalimidine is passed.

Exemplary ion exchange resins include, but are not limited to, Tulsion T 66 MP, Tulsion T-3825, Tulsion T 62 MP, and Tulsion T 62 having 2% crosslinking and an acid value of 4.8 to 5.0 meq/g resin. Such ion exchange resins are commercially available from Thermax. Further exemplary ion exchange resins include Amberlyst resins, such as Amberlyst 15, commercially available from Rohm and Haas.

The loading of the ion exchange resin can range from 5 wt % to 200 wt %, 10 wt % to 200 wt %, 5 wt % to 100 wt %, 10 wt % to 100 wt %, 5 wt % to 50 wt %, or 10 wt % to 50 wt %, based on wt % of the crude phthalimidine. A higher loading of ion exchange resin can allowed the used resin to be recycled through and two or more, or three or more cycles of purification of compound of formula (I).

Other suitable purification agents include, but are not limited to, acidic metal oxides including acidic silicas, acidic clays, acidic aluminas, acidic zeolites, sulfated zirconias, and the like. Acidic clays and acid-treated clays generally have Bronsted and Lewis acid sites and can be used for purifying. For example, clays, exemplified by maghnite, bentonite, attapulgite, sepiolite, the montmorillonite series of clays, the Filtrol series of clays, such as Filtrol 20, Filtrol 24, Filtrol 25, and Filtrol 62; and the like; can be treated with a mineral acid, such as for example, sulfuric acid, to obtain acidic clays that can be used as a purification agent. Acid-washed carbon may also be used. Examples of acid-washed carbons include for example, the Darco® series of acid-washed carbon, available in a variety of mesh sizes from 4 to 40 mesh from Aldrich Chemical Company. The acid-washed carbons are obtained by washing a carbon sample with an acid, such as phosphoric acid, sulfuric acid, hydrochloric acid, and the like. Due to the heterogeneous nature of these solid materials, a wide variety of acidic metal oxides having a range of acidity can be prepared. Further, the metal oxide can comprise one or more crystal or allotropic modifications. The acidic metal oxides are generally available commercially, or they can be prepared using methods known in the art. The particle size of the acidic metal oxide can vary, example from 60 mesh to 200 mesh.

The acidic metal oxide may also be pre-treated with a suitable agent prior to contacting the solution. Pre-treatment is generally done with an aqueous solution of a mineral acid (inorganic acid), such as for example, aqueous hydrochloric acid. The pre-treatment is done to remove trace levels of leachable metals that may be present in the acidic metal oxide. Acidic metal oxides, such as acidic alumina and acidic silica can be pre-treated prior to contacting with the solution.

Other purification agents include organosulfonic acids, preferably those having 2 or more carbon atoms. Examples of such organosulfonic acids include ethanesulfonic acid, propanesulfonic acid, butanesulfonic acid, octanesulfonic acid, dodecylbenzenesulfonic acid, and the like. Combinations of sulfonic acids can also be used. An organic solvent is generally used with the organosulfonic acids.

Other suitable purification agents include mineral acids, preferably in a polar organic solvent. Suitable mineral acids include hydrochloric acid, phosphoric acid, and the like. Mixtures of mineral acids can also be used. Suitable organic solvents to accompany the mineral acid include solvents comprising at least one functional group selected from the group consisting of a hydroxy group, a ketone carbonyl group, a carboxylic acid group, an ester group, a sulfoxide group, a nitrile group, an ether group, and a nitro group. Organic solvents that comprise at least one member selected from the group consisting of an organic hydroxy compound, an organic ketone, an organic amide, an organic sulfoxide, an organic ether, and an organic nitrile can be used. Each of these categories of solvents may further comprise more than one functional group, which may be the same or different from the other functional group(s). For example ethanol, ethylene glycol, and 2-ethoxyethanol may be used, either individually, or in any relative proportion, as suitable organic solvents. In certain embodiments, aliphatic alcohols having at least one hydroxy group can be used as the organic solvent. Suitable organic hydroxy compounds include aliphatic, cycloaliphatic and aromatic hydroxy compounds having at least one hydroxy group. The aliphatic hydroxy compounds include linear and branched aliphatic mono-hydroxy compounds, non-limiting examples of which are methanol, ethanol, isopropanol, n-butanol, sec-butanol, iso-butanol, tert-butanol, and the like. Mixtures of these compounds can also be used. Aliphatic dihydroxy compounds, such as the glycols, exemplified by ethylene glycol, propylene glycol, and the like may also be used. Non-limiting examples of aromatic hydroxy compounds include phenol, ortho-cresol, benzyl alcohol, and the like. Some examples of cycloaliphatic hydroxy compounds include cyclopentanol, cyclohexanol, cyclohexanediol, and the like. In certain embodiments, suitable organic hydroxy compounds include methanol, isopropanol, or any combination of methanol and isopropanol. Methanol is an exemplary organic solvent for use with a mineral acid to remove trace levels of metals. Organic ketones suitable for use as the organic solvent include acetone, 2-butanone, methyl ethyl ketone, diethyl ketone, methyl isopropyl ketone, and the like. In an embodiment, the organic solvent comprises acetone. Organic sulfoxides that may be used as the organic solvent include dimethylsulfoxide, methyl ethyl sulfoxide, diethyl sulfoxide, and the like. Non-limiting examples of organic nitriles include the aliphatic nitriles, such as acetonitrile, propionitrile, butyronitrile, hexanedinitrile, and the like. Examples of organic nitro compounds that may be used include nitromethane, nitroethane, and the like. In certain embodiments, the organic solvent is selected from the group consisting of methanol, ethanol, isopropanol, sec-butanol, phenol, acetone, butanone, formamide, 2-ethoxyethanol, and dimethylsulfoxide.

The impurities can also be removed by reacting with an organic anhydride. Some examples of organic anhydrides include phthalic anhydride, acetic anhydride, propionic anhydride, malonic anhydride, and the like. Organic acid chlorides can also be used.

A phthalimidine adduct can be precipitated from the crude phthalimidine solution after treatment with one or more purification agents. Precipitating the adducted from the solution treated with one or more purification agents can include one or more of: filtering the treated solution to remove at least one of the one or more purification agents; distilling the treated solution, optionally under reduced pressure, to remove at least a portion of the at least one solvent; cooling the treated solution to precipitate the phthalimidine adduct; filtering the treated solution to recover the precipitated phthalimidine adduct; and triturating the phthalimidine adduct. Triturating the phthalimidine adduct can include treating the precipitated phthalimidine adduct with a suitable triturating solvent or mixture of solvents (e.g., a 95:5 methanol-water mixture). The phthalimidine adduct can be precipitated at 10° C.

The distilling of the treated solution, optionally under reduced pressure, can be performed to remove excess solvent to affect the precipitation, and to recover solvents that can be recycled for further production and purification of phthalimidine compounds. In certain embodiments, the treated solution is distilled to remove 50% to 70% (e.g., 60%) of the solvent mixture. The distillation may be performed, for example, at 45° C. at 230-250 mbar pressure.

The treated solution may be cooled to a selected temperature to affect the precipitation of the phthalimidine adduct. For example, the treated solution can be cooled to 5° C. to 15° C. Preferably, the solution is cooled to 10° C. The cooled solution may be stirred, for example, for a selected time period (e.g., one hour) to precipitate the phthalimidine adduct.

The precipitated phthalimidine adduct can be recovered by any suitable method. For example, the precipitated adduct can be recovered by filtration, centrifugation, or a combination thereof.

The precipitated pthalimidine adduct can be triturated. As used herein, "trituration" is defined as mixing a solid with a trituration solvent and then isolating any undissolved material by filtration, centrifugation or a combination thereof. The trituration solvent is typically chosen such that the desired product has a low solubility in the solvent. During trituration, a portion of the solid such as impurities may dissolve in the solvent. The exact amount of the dissolved material depends on, among other things, the temperature at which the trituration is conducted and the amount of solvent used. Trituration can be conducted at a temperature above the freezing point of the trituration solvent and less than or equal to the boiling point of the trituration solvent. For example, trituration can be conducted at a temperature of 5° C. to 70° C. The time required for trituration varies depending on the trituration system and conditions and can be 5 minutes to 4 hours, for example. Suitable triturating solvents include, but are not limited to, polar solvents, non-polar solvents, and combinations of two or more of the foregoing solvents. Exemplary polar solvents include, but are not limited to, methanol, ethanol, isopropanol, propanol, chloroform, acetone, ethyl acetate, phenol, water, and combinations of two or more of the foregoing. Exemplary non-polar solvents include, but are not limited to, aromatic hydrocarbons having 6 to 14 carbons, aliphatic hydrocarbons having 5 to 8 carbons, non-polar chlorinated hydrocarbons, and combinations of two or more of the foregoing. Non-limiting examples of suitable aromatic hydrocarbon solvents include toluene, xylene, cumene, benzene and the like. Non-limiting examples of suitable aliphatic hydrocarbon solvents include hexane, cyclohexane, pentane, and the like. Non-limiting examples of non-polar chlorinated hydrocarbon solvents include 1,2-dichloroethane and the like. Non-limiting examples of suitable triturating solvents comprising mixtures include methanol:toluene, methanol:water, ethyl acetate:toluene, ethyl acetate: 1,2-dichloroethane, acetone: 1,2-dichloroethane, acetone:toluene, acetone:hexane, isopropanol:toluene, acetone:water, and isopropanol:water. The volume ratios (v:v) of the solvent mixtures can be 1:99 to 99:1. Exemplary solvent mixtures include, but are not limited to, methanol:toluene (2:98, v:v), methanol:toluene (13:87, v:v), methanol:water (90:10, v:v), and methanol:water (95:5, v:v). In certain embodiments, the phthalimidine adduct is triturated in methanol:water (95:5, v:v) at 60° C. for 3 hours, and 10° C. for 1 hour. In certain embodiments, the phthalimidine adduct is not triturated.

The phthalimidine adduct can be a phthalimidine-solvent adduct, such as a phthalimidine-methanol adduct. The nature of the adduct and the relative stoichiometry of the 2-hydrocarbyl-3,3-bis(4-hydroxyaryl)phthalimidine compound and the organic solvent molecules constituting the adduct varies depending upon the structure of the 2-hydrocarbyl-3,3-bis (4-hydroxyaryl)phthalimidine and the structure and nature of the organic solvent. In the case of 2-phenyl-3,3-bis(4-hydroxyphenyl)phthalimidine (PPPBP), the adducts can have a molar ratio of 1:x of the PPPBP and the organic solvent, respectively; wherein "x" has a value of from 0.5 to 2. The organic solvent can be any of the solvents described previously herein. In certain embodiments, the organic solvent that can form an adduct is selected from the group consisting of methanol, ethanol, isopropanol, sec-butanol, phenol, acetone, butanone, formamide, methyl amine, isopropyl amine, formamide, dimethylsulfoxide, and aniline. For example, methanol and PPPBP can form an adduct having the formula 1 PPPBP:1 $CH_3OH$. On the other hand, acetone can form an adduct with PPPBP having the formula 1 PPPBP:0.5 acetone. The organic solvent in these adducts is tightly bound to the PPPBP molecule as seen from the fact that these materials have relatively high decomposition temperatures. For example, the 1 PPPBP:1 $CH_3OH$ adduct decomposes at a temperature of 150° C. at ambient pressure.

The purified compound of formula (I) can be recovered from the phthalimidine adduct by washing the phthalimidine adduct with hot water, followed by drying. Washing the adduct with hot water can include washing the adduct over a filter, or re-slurrying the adduct and filtering. The wash water may be at a temperature of 90° C. to 100° C., for example. The drying may be performed using a hot air oven, for example. The drying may be performed at a temperature of 100° C. to 110° C., for example. The drying may be performed at the eleveated temperature for a time period of 8 hours to 10 hours, for example. The purified phthalimidine compound can be used as a monomer for synthesis of copolymers, for example.

The one or more solvents used in the disclosed methods can be recycled and used again through multiple cycles of production and purification of compounds of formula (I). Solvents may be recovered using distillation, for example. In certain embodiments, at least a portion of the disclosed methods are a closed loop system with respect to solvent use for at least two cycles of production and purification of a compound of formula (I). In certain embodiments, the disclosed methods are a closed loop system with respect to solvent use for at least three cycles of production and purification of a compound of formula (I). For example, multiple crops of purified compound of formula (I) can be prepared and recovered without addition of solvent (e.g., methanol, toluene) to the system.

Accordingly, one or more of the filtrates generated in the purification process can be recovered and recycled through one or more of the purification steps to recover solvents, and optionally additional purified compound of formula (I). For example, mother liquor obtained (e.g., from methanol-water wash steps, trituration steps, or a combination thereof) can be subjected to distillation to recover solvent. Mother liquor obtained after precipitations (e.g., crystallization of the phthalimidine adduct) can be subjected to distillation to recover solvent (e.g., methanol, toluene, or a combination thereof). Filtrates obtained after recycling or regeneration of purification agents can be recovered and subjected to distillation to recover solvent.

Solvent recovery may be 80% or greater, 85% or greater, 90% or greater, or 95% or greater. Solvent recovery may be 80%, 81%, 82%, 83%, 84%, 85%, 86%, 87%, 88%, 89%, 90%, 91%, 92%, 93%, 94%, 95%, or greater.

One or more purification agents used in the disclosed methods can be recycled and used again over two or more cycles of purification of phthalimidine compound. The recycled purification agent can be an ion exchange resin. For example, an ion exchange resin can be washed with a selected solvent (e.g., methanol, preferably cold methanol) and used again to treat a solution of crude phthalimidine. The concentration of aminophenol impurity in the crude phthalimidine may control the number of cycles of operation of the purification agent (e.g., ion exchange resin). For example, in certain embodiments, the purification agent (e.g., ion exchange resin) can be recycled two or more times where the aminophenol impurity concentration in the crude pthalimidine is 1,800 ppm or less. In certain embodiments, the purification agent (e.g., ion exchange resin) can be recycled one time where the aminophenol impurity concentration in the crude phthalimidine is greater than 1,800 ppm.

An exemplary process for recycling a purification agent, such as an ion exchange resin, includes recovering the purification agent after treatment of a solution of crude phthalimidine, washing the purification agent (e.g., with cold methanol), drying the purification agent, and re-using the purification agent. The exemplary recycling process may be repeated at least one time, at least two times, or greater, depending on the performance of the purification agent after each recycling.

The purity of a compound of formula (I) recovered using recycled purification agent in accordance with the disclosed methods may be greater than or equal to 99.80%, greater than or equal to 99.85%, or greater than or equal to 99.90%. Purification agents (e.g., ion exchange resin) recycled at least one time, at least two times, or greater, may give the purities of greater than or equal to 99.80%, greater than or equal to 99.85%, or greater than or equal to 99.90%. The amount of aminophenol impurity in the purified phthalimidine compound may be 10% or less of the initial amount in the crude phthalimidine when using a purification agent recycled at least one time, at least two times, or greater.

One or more purification agents used in the disclosed methods can be regenerated and used again over two or more cycles of purification of phthalimidine compounds. The regenerated purification agent can be an ion exchange resin. An exemplary regeneration process includes treatment of a spent purification agent with an acid in one or more solvents; filtration of the resultant regenerated purification agent; and washing of the regenerated purification agent with one or more solvents (e.g., an organic solvent followed by an aqueous solvent). For example, a spent purification agent (e.g., an ion exchange resin) can be regenerated by treating the spent resin with a toluene-methanol mixture and 35% concentrated hydrochloric acid. After recovery of the regenerated purification agent (e.g., by filtration, on a sintered funnel for example), the agent can be washed and dried for re-use. The washing of the regenerated purification agent can be conducted until the pH of the washings are neutral. The volumes of organic solvent (e.g., toluene, methanol, or a combination thereof) used to regenerate the purification agent can be 9 volumes. The volumes of acid (e.g., 35% conc. hydrochloric acid) used to regenerate the purification agent can be 4 volumes. The volumes of organic solvent (e.g., methanol, toluene, or a combination thereof) used to wash the regenerated purification agent can be 1 volume. The volume of aqueous solvent used to wash the regenerated purification agent can be 2 volumes.

Preferably, solvents used in the regeneration processes can be recovered and at least a portion of the solvents (e.g., methanol, toluene, or a combination thereof) recycled for further use in accordance with the disclosed methods of purifying phthalimidine compounds of formula (I). The solvent recovery from the regeneration process (e.g., recovery of methanol, toluene, or a combination thereof) can be 80% or greater, 85% or greater, or 90% or greater.

For example, an ion exchange resin (e.g., beads of ion exchange resin) can be regenerated by treatment with 4 volumes hydrochloric acid and 9 volumes of a solvent mixture of methanol-toluene mixture (e.g., a 3.5:1 methanol:toluene mixture). After stirring the resin in the regenerating solution for 3-4 hours at room temperature, the resin can be filtered and washed with 1 volume of a methanol-toluene mixture (e.g., a 3.5:1 methanol:toluene mixture), followed by 2 volumes of water, preferably until the pH of the washings are neutral. The resin can then be washed with pure methanol and dried for re-use. The methanol and toluene solvents used in the process can be collected and distilled for re-use.

The purity of a compound of formula (I) recovered using regenerated purification agent in accordance with the disclosed methods may be greater than or equal to 99.80%, greater than or equal to 99.85%, or greater than or equal to 99.90%. Purification agents (e.g., ion exchange resin) regenerated at least one time, at least two times, or greater, may give the purities of greater than or equal to 99.80%, greater than or equal to 99.85%, or greater than or equal to 99.90%. The amount of aminophenol impurity in the purified phthalimidine compound may be 3% or less of the initial amount in the crude phthalimidine when using a purification agent regenerated at least one time, at least two times, or greater.

The acidity of a purification agent (e.g., an acidic ion exchange resin) can be regenerated to 90% or greater, or 95% or greater of its original acidity, as measured by milliequivalents of hydronium ion per gram of agent (e.g., ion exchange resin).

Copolymers can be prepared including repeating units derived from the purified phthalimidine compounds of formula (I). The copolymer may be a copolycarbonate including repeating units of formula (1),

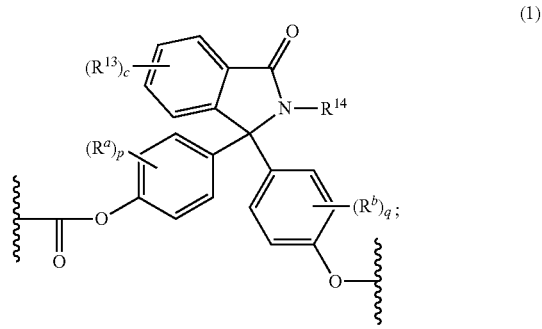

(1)

wherein $R^{13}$ at each occurrence is independently a halogen or a $C_1$-$C_6$ alkyl group; $R^{14}$ is independently a $C_1$-$C_6$ alkyl, phenyl, or phenyl substituted with up to five halogens or $C_1$-$C_6$ alkyl groups; $R^a$ and $R^b$, at each occurrence, are each independently a halogen, $C_1$-$C_{12}$ alkyl, $C_1$-$C_{12}$ alkenyl, $C_3$-$C_8$ cycloalkyl, or $C_1$-$C_{12}$ alkoxy; c is independently 0 to 4; and p and q are each independently 0 to 4. In a specific embodiment, $R^{14}$ is a $C_1$-$C_6$ alkyl or phenyl group. In still another embodiment, $R^{14}$ is a methyl or phenyl group. In another specific embodiment, c is 0; p is 0; and q is 0.

The polycarbonate may include further repeating units of formula (2):

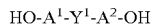
(2)

wherein each of the $A^1$ and $A^2$ is a monocyclic divalent aryl group and $Y^1$ is a bridging group having one or two atoms that separate $A^1$ and $A^2$. For example, one atom may separate $A^1$ from $A^2$, with illustrative examples of these groups including —O—, —S—, —S(O)—, —S(O)$_2$—, —C(O)—, methylene, cyclohexyl-methylene, 2-[2.2.1]-bicycloheptyl-idene, ethylidene, isopropylidene, neopentylidene, cyclohexylidene, cyclopentadecylidene, cyclododecylidene, and adamantylidene. The bridging group of $Y^1$ may be a hydrocarbon group such as methylene, cyclohexylidene, or isopropylidene.

The repeating units of formula (2) may be derived from a dihydroxy monomer unit of formula (3):

$$HO-A^1-Y^1-A^2-OH \qquad (3)$$

wherein $A^1$, $A^2$, and $Y^1$ are as defined above.

The polycarbonate may include further repeating units of formula (4):

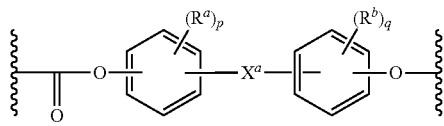
(4)

wherein $R^a$ and $R^b$ are each independently halogen, $C_1$-$C_{12}$ alkyl, $C_1$-$C_{12}$ alkenyl, $C_3$-$C_8$ cycloalkyl, or $C_1$-$C_{12}$ alkoxy; p and q are each independently 0 to 4; and $X^a$ is a bridging group between the two arylene groups. $X^a$ may be a single bond, —O—, —S—, —S(O)—, —S(O)$_2$—, —C(O)—, or a $C_1$-$C_{18}$ organic group. The $C_1$-$C_{18}$ organic bridging group may be cyclic or acyclic, aromatic or non-aromatic, and can optionally include halogens, heteroatoms (e.g., oxygen, nitrogen, sulfur, silicon, or phosphorous), or a combination thereof. The $C_1$-$C_{18}$ organic group can be disposed such that the $C_6$ arylene groups connected thereto are each connected to a common alkylidene carbon or to different carbons of the $C_1$-$C_{18}$ organic bridging group. The bridging group $X^a$ and the carbonate oxygen atoms of each $C_6$ arylene group can be disposed ortho, meta, or para (specifically para) to each other on the $C_6$ arylene group. Exemplary $X^a$ groups include, but are not limited to, methylene, ethylidene, neopentylidene, isopropylidene, cyclohexylmethylidene, 1,1-ethene, 2-[2.2.1]-bicycloheptylidene, cyclohexylidene, cyclopentylidene, cyclododecylidene, and adamantylidene.

In certain embodiments, p and q are each 1; $R^a$ and $R^b$ are each a $C_1$-$C_3$ alkyl group, specifically methyl, disposed meta to the oxygen on each ring; and $X^a$ is isopropylidene. In certain embodiments, p and q are both 0; and $X^a$ is isopropylidene.

In certain embodiments, $X^a$ may have formula (5):

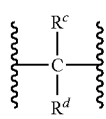
(5)

wherein $R^c$ and $R^d$ are each independently hydrogen, halogen, alkyl (e.g., $C_1$-$C_{12}$ alkyl), cycloalkyl (e.g., $C_3$-$C_{12}$ cycloalkyl), cycloalkylalkyl (e.g., $C_3$-$C_{12}$-cycloalkyl-$C_1$-$C_6$-alkyl), aryl (e.g., $C_6$-$C_{12}$ aryl), arylalkyl (e.g., $C_6$-$C_{12}$-aryl-$C_1$-$C_6$-alkyl), heterocyclyl (e.g., five- or six-membered heterocyclyl having one, two, three, or four heteroatoms independently selected from nitrogen, oxygen, and sulfur), heterocyclylalkyl (e.g., five- or six-membered heterocyclyl-$C_1$-$C_6$-alkyl), heteroaryl (e.g., five- or six-membered heteroaryl having one, two, three, or four heteroatoms independently selected from nitrogen, oxygen, and sulfur), or heteroarylalkyl (e.g., five- or six-membered heteroaryl-$C_1$-$C_6$-alkyl), wherein said alkyl, cycloalkyl, cycloalkylalkyl, aryl, arylalkyl, heterocyclyl, heterocyclylalkyl, heteroaryl, and heteroarylalkyl are each independently unsubstituted or substituted (e.g., substituted with 1 to 3 substituents independently selected from the group consisting of —OH, —NH$_2$, —NO$_2$, —CN, halo, $C_1$-$C_4$-alkyl, $C_1$-$C_4$-alkoxy-$C_1$-$C_4$-alkyl, halo-$C_1$-$C_4$-alkyl, halo-$C_1$-$C_4$-alkoxy-$C_1$-$C_4$-alkyl, hydroxy-$C_1$-$C_4$-alkyl, amino-$C_1$-$C_4$-alkyl, $C_1$-$C_4$-alkylamino-$C_1$-$C_4$-alkyl, di($C_1$-$C_4$-alkyl)amino-$C_1$-$C_4$-alkyl, azido-$C_1$-$C_4$-alkyl, cyano-$C_1$-$C_4$-alkyl, $C_1$-$C_4$-alkoxy, halo-$C_1$-$C_4$-alkoxy, $C_1$-$C_4$-alkoxy-$C_1$-$C_4$-alkoxy, $C_2$-$C_4$-alkenyl, and $C_2$-$C_4$-alkynyl). In certain embodiments, $R^c$ and $R^d$ are each independently hydrogen or $C_1$-$C_8$ alkyl. In certain embodiments, $R^c$ and $R^d$ are each methyl. Exemplary groups of formula (5) include, but are not limited to, methylene, ethylidene, neopentylidene, and isopropylidene.

In certain embodiments, $X^a$ may have formula (6):

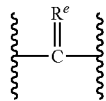
(6)

wherein $R^e$ is a divalent $C_1$-$C_{31}$ group. In certain embodiments, $R^e$ is a divalent hydrocarbyl (e.g., a $C_{12}$-$C_{31}$ hydrocarbyl), a cycloalkylidene (e.g., a $C_5$-$C_{18}$ cycloalkylidene), a cycloalkylene (e.g., a $C_5$-$C_{18}$ cycloalkylene), a heterocycloalkylidene (e.g., a $C_3$-$C_{18}$ heterocycloalkylidene), or a group of the formula —B$^1$-G-B$^2$— wherein B$^1$ and B$^2$ are the same or different alkylene group (e.g., a $C_1$-$C_6$ alkylene group) and G is a cycloalkylidene group (e.g., a $C_3$-$C_{12}$ cycloalkylidene group) or an arylene group (e.g., a $C_6$-$C_{16}$ arylene group), wherein said hydrocarbyl, cycloalkylidene, cycloalkylene, and heterocycloalkylidene are each independently unsubstituted or substituted (e.g., substituted with 1 to 3 substituents independently selected from the group consisting of —OH, —NH$_2$, —NO$_2$, —CN, halo, $C_1$-$C_4$-alkyl, $C_1$-$C_4$-alkoxy-$C_1$-$C_4$-alkyl, halo-$C_1$-$C_4$-alkyl, halo-$C_1$-$C_4$-alkoxy-$C_1$-$C_4$-alkyl, hydroxy-$C_1$-$C_4$-alkyl, amino-$C_1$-$C_4$-alkyl, $C_1$-$C_4$-alkylamino-$C_1$-$C_4$-alkyl, di($C_1$-$C_4$-alkyl)amino-$C_1$-$C_4$-alkyl, azido-$C_1$-$C_4$-alkyl, cyano-$C_1$-$C_4$-alkyl, $C_1$-$C_4$-alkoxy, halo-$C_1$-$C_4$-alkoxy, $C_1$-$C_4$-alkoxy-$C_1$-$C_4$-alkoxy, $C_2$-$C_4$-alkenyl, and $C_2$-$C_4$-alkynyl). Exemplary groups of formula (6) include, but are not limited to, 2-[2.2.1]-bicycloheptylidene, cyclohexylidene, cyclopentylidene, cyclododecylidene, and adamantylidene.

The repeating structural units of formula (4) may be derived from a dihydroxy monomer unit of formula (7):

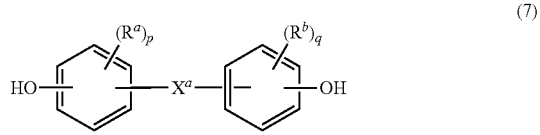

wherein $X^a$, $R^a$, $R^b$, p, and q are as defined above. In certain embodiments, p and q are both 0, and $X^a$ is isopropylidene.

Exemplary monomers for inclusion in the polycarbonate include, but are not limited to, 4,4'-dihydroxybiphenyl, 1,1-bis(4-hydroxyphenyl)methane, bis(4-hydroxyphenyl) acetonitrile, bis(4-hydroxyphenyl)phenylmethane, bis(4-hydroxyphenyl)-1-naphthylmethane, 1,1-bis(4-hydroxyphenyl)ethane, 1,2-bis(4-hydroxyphenyl)ethane, 1,1-bis(4-hydroxyphenyl)-1-phenylethane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 1,1-bis(4-hydroxyphenyl)propane, 1,1-bis(4-hydroxy-t-butylphenyl)propane, 2,2-bis(4-hydroxyphenyl)propane ("bisphenol-A" or "BPA"), 2-(4-hydroxyphenyl)-2-(3-hydroxyphenyl)propane, 2,2-bis(4-hydroxy-2-methylphenyl)propane, 2,2-bis(3-methyl-4-hydroxyphenye propane, 2,2-bis(3-ethyl-4-hydroxyphenyl) propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenye propane, 2,2-bis(3-cyclohexyl-4-hydroxyphenyl)propane, 2,2-bis(3-allyl-4-hydroxyphenyl) propane, 2,2-bis(3-methoxy-4-hydroxyphenyl)propane, 2,2-bis(4-hydroxy-3-bromophenyl)propane, 2,2-bis(4-hydroxyphenyl)hexafluoropropane, 1,1-bis(4-hydroxyphenyl)n-butane, 2,2-bis(4-hydroxyphenyl)butane, 3,3-bis(4-hydroxyphenyl)-2-butanone, 1,1-bis(4-hydroxyphenyl)isobutene, trans-2,3-bis(4-hydroxyphenyl)-2-butene, 1,6-bis(4-hydroxyphenyl)-1,6-hexanedione, 2,2-bis(4-hydroxyphenyl)octane, 1,1-bis(hydroxyphenyl)cyclopentane, 1,1-bis(4-hydroxyphenyl)cyclohexane, 1,1-bis(4-hydroxy-3-methylphenyl)cyclohexane, 1,1-bis(4-hydroxyphenyl)cyclododecane, 2,2-bis(4-hydroxyphenyl)adamantane, (alpha, alpha'-bis(4-hydroxyphenyl)toluene, 4,4'-dihydroxybenzophenone, 2,7-dihydroxypyrene, bis(4-hydroxyphenyl)ether, ethylene glycol bis(4-hydroxyphenyl)ether, bis(4-hydroxyphenyl)sulfide, bis(4-hydroxyphenyl)sulfoxide, bis(4-hydroxyphenyl)sulfone, bis(4-hydroxyphenyl)diphenylmethane, 1,6-dihydroxynaphthalene, 2,6-dihydroxynaphthalene, 6,6'-dihydroxy-3,3,3',3'-tetramethylspiro(bis)indane ("spirobiindane bisphenol"), 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, 2,7-dihydroxycarbazole, 2-phenyl-3,3-bis(4-hydroxyphenyl)phthalimidine (also referred to as 3,3-bis(4-hydroxyphenyl)-2-phenylisoindolin-1-one or "PPPBP"), 9,9-bis(4-hydroxyphenyl)fluorene, and bisphenol isophorone (also referred to as 4,4'-(3,3,5-trimethylcyclohexane-1,1-diyl)diphenol or "BPI"), 1,1-bis(4-hydroxy-3-methylphenyl)cyclohexane ("DMBPC"), tricyclopentadienyl bisphenol (also referred to as 4,4'-(octahydro-1H-4,7-methanoindene-5,5-diyl)diphenol), 2,2-bis(4-hydroxyphenyl)adamantane ("BCF"), 1,1-bis(4-hydroxyphenyl)-1-phenyl ethane ("BPAP"), and 3,3-bis(4-hydroxyphenyl)phthalide, or any combination thereof.

Other dihydroxy monomer units that may be used include aromatic dihydroxy compounds of formula (8):

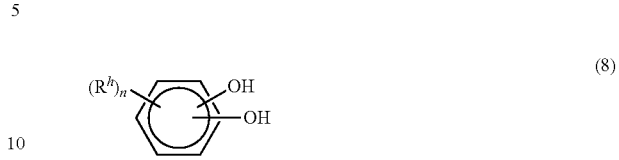

wherein each $R^h$ is independently a halogen atom, a $C_1$-$C_{10}$ hydrocarbyl such as a $C_1$-$C_{10}$ alkyl group, or a halogen substituted $C_1$-$C_{10}$ hydrocarbyl such as a halogen-substituted $C_1$-$C_{10}$ alkyl group, and n is 0 to 4. The halogen, when present, is usually bromine.

Examples of aromatic dihydroxy compounds represented by formula (8) include, but are not limited to, resorcinol, substituted resorcinol compounds (e.g., 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol), catechol, hydroquinone, substituted hydroquinones (e.g., 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, and the like, as well as combinations thereof.

EXAMPLES

HPLC analysis was generally carried out by using an HPLC instrument equipped with a $C_{18}$ (reverse phase) column and a Photo Diode Array detector. A solvent mixture of methanol, water, and acetonitrile of varying relative proportions was used. Area percent assay was computed from the area value for each peak detected in the chromatogram divided by the total area from all peaks detected. To measure weight percent assay, calibration curves for para, para-PPPBP, ortho, para-PPPBP, AP, and phenolphthalein were first generated. Then the weight percent of a given component in a sample was calculated using these calibration curves.

The acidity of the acidic ion exchange resin, expressed as milliequivalents of $H^+$ per gram of resin (meq/g), was determined by a method known in the art. The resin was treated with 20 weight percent aqueous sodium chloride solution, and the liberated hydrochloric acid was titrated against aqueous (Aq.) sodium hydroxide (NaOH).

Example 1. Preparation of Crude PPPBP

A four necked round bottom flask equipped with overhead stirrer, thermowell, condenser fitted with a Dean-Stark apparatus, and inlet for nitrogen was charged with aniline (117.0 g) and HCl (33.0 mL, 35% conc.). The resulting mixture was allowed to stir for 1 h, followed by addition of phenolphthalein (100.0 g). The reaction mixture was then heated slowly to 154° C. to remove water via the Dean-Stark trap, and subsequently allowed to continue stirring at 154° C. for 22 h. At this point, a sample of the reaction mixture was analyzed by HPLC for aminophenol (AP) and phenolphthalein (PP) content (AP=2100 ppm; PP<1%). The reaction mixture was then cooled to 120° C., whereupon water (300 mL) and HCl (154 mL, 35% conc.) were added. The reaction mixture was allowed to stir for 1 h at this temperature, then cooled to rt. The resulting solid was filtered and washed with DI water until the washings were acid free. The solid was then dried in a centrifuge until the moisture content was less than 20% (as measured by KF titration). Yield of PPPBP: ~99% (dry weight basis), purity=98%.

Example 2. Purification of PPPBP with 9 Volumes of Toluene/Methanol and Tulsion T 62 MP 136 g crude PPPBP (AP=1500±200 ppm; PP<1%; moisture ~26%) was weighed onto a Buchner funnel. The solid was washed with a methanol/water mixture (100 mL; 90:10; pre-cooled to 10° C.). The solid (moisture content<4%; measured by KF titration) was collected and stirred in a mixture of methanol (700 mL) and toluene (200 mL). Urea (5 g) was added to the suspension, and the resulting mixture was heated at 60° C. for 30 min to 1 h. To the resulting purple colored solution was added normal grade activated carbon (5 g), while stirring at 60° C. for 1 h. The activated carbon was filtered and washed with 50 mL of hot methanol. The filtrate was collected in a round bottom flask, and 50 g of dried 2% cross-linked acidic ion exchange resin (Tulsion T 62 MP (Thermax); acidity of the fresh IER=4.8-5.0 meq/g) was added. This mixture was stirred at 60° C. for 2 h. (Stirrer blade should be adjusted just below the surface of the solution in order to avoid breaking of IER beads.) The mixture was filtered to remove the ion exchange resin, which was washed with 50 mL hot methanol.

The resulting pale yellow colored solution was concentrated under reduced pressure to remove 60% of the solvent (45° C., 230 mbar). The resulting solution was cooled slowly to 10° C. and maintained at that temperature for 30 min to 1 h with stirring. A white solid subsequently crystallized and was collected. The solid was transferred into a round bottom flask, which was charged with a mixture of methanol and water (200 mL; 95:5). The mixture was allowed to stir at 60° C. for 3 h and then cooled to 10° C. and maintained at that temperature for 1 h with stirring. The solid was collected via filtration (filtrate collected for mother liquor recycle) and washed with 100 mL water (pre-heated to 100° C.). The resulting product was dried at 100-110° C. for 14 h. PPPBP was obtained as a white amorphous powder (94% yield).

The filtrate mother liquor (~400 mL, containing 3-4% of crude PPPBP) was heated at 60° C. for 1 h, followed by treatment with activated carbon and ion exchange resin as done for crop 1 of the PPPBP. The resulting solution was concentrated under reduced pressure to remove up to 4 volumes of the solvent (45° C., 230 mbar) to obtain additional crops of pure PPPBP.

Example 3. Purification of PPPBP with 9 Volumes of Toluene/Methanol and Tulsion T 66 MP The procedure of Example 2 was utilized, but with Tulsion T 66 MP (Thermax) (acid meq/g of the fresh IER: 4.8-5.0 meq/g) as the ion exchange resin. PPPBP was obtained as a white amorphous powder (95% yield).

Example 4. Purification of PPPBP with 24 Volumes of Methanol and Tulsion T 62 MP 136 g crude PPPBP (with AP=1500±200 ppm; PP<1%; moisture ~26%) was weighed onto a Buchner funnel. The solid was washed with a mixture of methanol and water (100 mL; 90:10; pre-cooled to 10° C.). The solid (moisture content<4%; measured by KF titration) was collected and stirred in methanol (2.4 L). Urea (10 g) was added to the suspension, and the resulting mixture was heated at 60° C. for 30 min to 1 h. To the resulting purple colored solution was added normal grade activated carbon (5 g), while stirring at 60° C. for 1 h. The activated carbon was filtered and washed with 50 mL of hot methanol. The filtrate was collected in a round bottom flask, and 50 g of dried 2% cross-linked acidic ion exchange resin (Tulsion T 62 MP (Thermax); acidity of the fresh IER=4.8-5.0 meq/g) was added. This mixture was stirred at 60° C. for 2 h. (Stirrer blade should be adjusted just below the surface of the solution in order to avoid breaking of IER beads.) The mixture was filtered to remove the ion exchange resin, which was washed with 50 mL hot methanol.

The resulting pale yellow colored solution was cooled slowly to 10° C. and maintained at that temperature for 30 min to 1 h with stirring. A white solid subsequently crystallized and was collected. The solid was transferred back into the round bottom flask, which was charged with methanol (100 mL) at 10° C. for a slurry wash. The solid was collected via filtration and washed with 100 mL water (pre-heated to 100° C.). The resulting product was dried at 100-110° C. for 14 h. PPPBP was obtained as a white amorphous powder (75% yield).

Example 5. Purification of PPPBP with 24 Volumes of Methanol and Tulsion T 66 MP The procedure of Example 4 was utilized, but with Tulsion T 66 MP (Thermax) (acid meq/g of the fresh IER: 4.8-5.0 meq/g) as the ion exchange resin. PPPBP was obtained as a white amorphous powder (73% yield).

Example 6. Purification of PPPBP with 17 Volumes of MeOH (14PLAS0090)

120 g crude PPPBP (AP=2100±200 ppm; PP<1%; moisture ~26%) was weighed onto a Buchner funnel. The solid was washed with cold methanol (100 mL). The solid (moisture content<4%; measured by KF titration) was collected and stirred in methanol (1.7 L). Urea (10 g) was added to the suspension, and the resulting mixture was heated at 60° C. for 1 h. To the resulting purple colored solution was added activated carbon (5 g), while stirring at 60° C. for 1 h. The activated carbon was removed via filtration. The filtrate was collected in a round bottom flask, and 50 g of dried 2% cross-linked acidic ion exchange resin (Rohm and Haas or Tulsion or Thermax; acidity of the fresh IER=4.8-5.0 meq/g) was added. This mixture was stirred at 60° C. for 1 h. The mixture was filtered to remove the ion exchange resin.

The filtrate was cooled to 10° C. and maintained at that temperature for 1 h with stirring. A white solid subsequently crystallized and was collected, washed with hot water, and dried at 100-110° C. for 14 h to yield PPPBP (90 g, 90% yield; purity=99.9%; APHA=18) [phenolphthalein (<500 ppm) and aminophenol impurity (<50 ppm) are within required spec].

From the filtrate, 400 mL methanol was recovered via distillation. To the remaining filtrate (1450 mL/~14 Volumes with respect to PPPBP), 300 mL of fresh methanol and 1.6 g urea were added, and this mixture was used for the next batch of crude PPPBP purification. Similar mother liquor recycles were achieved for more than 5 cycles of purification.

Example 7. Purification of PPPBP with Alkaline Solution and Activated Carbon Sodium hydroxide (10.5 g) was dissolved in water (240 mL). 50 g crude PPPBP was added and the resulting mixture was allowed to stir at rt for 1 h. Insoluble material was then removed via filtration. An aqueous solution of sodium hydroxide (3.5 g of NaOH in 24 mL water) was added at rt and subsequently the mixture was allowed to stir for 15 min. Activated carbon (5 g; special grade) was added to the PPPBP solution, which was then allowed to stir for 1 h at rt. The activated carbon was removed via filtration. This procedure was repeated until the AP and PP impurity levels were reduced to <50 ppm (as judged by HPLC).

The filtrate from above was filtered through a 1-micron filter cloth and added dropwise to a 5% HCl solution (48.8 mL HCl (35%) in 266 mL water). The resulting mixture was allowed to stir until the pink color of the alkaline PPPBP disappeared (pH=2). The resulting solid was collected via filtration and washed with DI water until the washings were acid free. The semi-crude PPPBP was then dried at 120° C. for 14 h.

40 g of the dry semi-crude PPPBP was added to a mixture of methanol and water (90:10, 160 mL) in a round bottom flask fitted with a reflux condenser. The subsequent mixture was heated at reflux with stirring for 1 h. The solution was then cooled to 10° C. and maintained at that temperature for 20-25 min. The resulting solid was collected and transferred into a round bottom flask with 400 mL of water. This mixture was then heated to 100° C., followed by filtration. The solid product obtained was dried at 100-110° C. for 24 h to give PPPBP (90% yield).

Example 8. PPPBP Purification with PTSA and Activated Carbon

Crude PPPBP can also be purified using a mixture of methanol/acetone/water (0.9:0.9:0.2; 6 volumes) in the presence of para-toluenesulfonic acid at room temperature. This method utilizes normal grade activated carbon for the purification process as well. Table 1 summarizes the new experimental methods for the purification of PPPBP in comparison to the control method (Example 7).

TABLE 1

Results of PPPBP purification procedures

| Ex. | Solvent ratio | Solvent | Volumes | Urea | Ion Exchange Resin | AP (ppm) | Yield (%) |
|---|---|---|---|---|---|---|---|
| 2 | 1:3.5 | Toluene:Methanol | 9 | 5% | Tulsion T 62 MP | nd | 94.3 |
| 3 | 1:3.5 | Toluene:Methanol | 9 | 5% | Tulsion T 66 MP | 63 | 95 |
| 4 | — | Methanol | 24 | 10% | Tulsion T 62 MP | 23 | 75 |
| 5 | — | Methanol | 24 | 10% | Tulsion T 66 MP | 42 | 73 |
| 6 | — | Methanol | 17 | 10% | Tulsion or Thermax | <50 | 90 |
| 7 | — | Aq. NaOH | 7 | — | — | 35 | 90 |

Example 9. Screen of Solvents as Alternatives to Urea

A series of solvents were investigated as potential replacements for urea in the purification process of Example 6. Table 2 shows the results of using these solvents as additives in the purification process. In all cases, crystallization of the PPPBP-MeOH adduct could not be controlled and stabilized as easily as with urea.

TABLE 2

Screening of solvents as alternatives to urea

| Solvent | Loading (wt % relative to PPPBP) | Results |
|---|---|---|
| DMF | 10% | Dissolved at 60° C.; crystallized out gradually upon cooling |
| DMSO | 10% | Dissolved at 60° C.; crystallized out at 2 hours |
| Ethyl Acetate | 10% | Dissolved at 60° C.; crystallized out at 30 min |
| Ethylene Glycol | 10% | Dissolved at 60° C.; crystallized out gradually upon cooling |

Example 10. PPPBP Purification with Recycled Mother Liquor

The procedure of Example 6 was utilized to purify crude PPPBP containing 1% phenolphthalein (PP) and 1890 ppm aminophenol (AP). The mother liquor (ML) of the first purification of PPPBP was re-introduced into the purification procedure to obtain subsequent batches of purified PPPBP. Table 3 shows that there is no appreciable change in purity of each batch of purified PPPBP for which recycled ML is used. In addition, the composition of the ML remained unchanged after four recycles (Table 4).

TABLE 3

Purification of PPPBP with recycled mother liquor

| | AP (%) | PP (%) | PPPBP purity (%) | Recovery (%) |
|---|---|---|---|---|
| PPPBP 1 | nd | 0.018 | 99.9 | 92 |
| PPPBP 2 (1st recycle of ML) | nd | 0.0169 | 99.9 | 92 |
| PPPBP 3 (2nd recycle of ML) | 0.0007 | 0.0174 | 99.9 | 92 |
| PPPBP 4 (3rd recycle of ML) | 0.0005 | 0.0152 | 99.9 | 92 |

TABLE 4

Mother liquor composition

| Recycle of ML | AP (%) | PP (%) | other impurities (%) | PPPBP purity (%) |
|---|---|---|---|---|
| ML 1 | nd | 6.2 | 0.61 | 93.2 |
| ML 2 | nd | 6.2 | 0.6 | 93.2 |

TABLE 4-continued

Mother liquor composition

| Recycle of ML | AP (%) | PP (%) | other impurities (%) | PPPBP purity (%) |
|---|---|---|---|---|
| ML 3 | nd | 6.4 | 0.61 | 93.1 |
| ML 4 | nd | 6.4 | 0.62 | 93.1 |

In addition, Table 5 shows the impurity profile of the purified PPPBP batches. Each impurity is represented by its retention time (via HPLC). As it is demonstrated here, there are no increases in impurities associated with recycling of the mother liquors.

TABLE 5

Impurity profile of purified PPPBP

| | HPLC Retention Time | | | |
|---|---|---|---|---|
| | 17.5 (%) | 17.8 (%) | 20.3 (%) | 21.6 (%) |
| PPPBP crude | 0.0298 | 0.0285 | 0.065 | 0.0967 |
| PPPBP 1 | 0.0098 | 0.0025 | 0.0051 | 0.0178 |
| PPPBP 2 (1$^{st}$ recycle of ML) | 0.0102 | 0.0032 | 0.006 | 0.0189 |
| PPPBP 3 (2$^{nd}$ recycle of ML) | 0.0089 | 0.0019 | 0.0046 | 0.0201 |
| PPPBP 4 (3$^{rd}$ recycle of ML) | 0.011 | 0.0034 | 0.0072 | 0.0196 |

An additional experiment was carried out wherein the crude PPPBP was mixed with an amount of phenolphthalein equivalent to that which would be present after a 20$^{th}$ recycling of the ML. Purification was achieved using the procedure of Example 6, resulting in a yield of 90% PPPBP with 99.9% purity and only 0.0319% PP. These values were similar to what was obtained with the initial purifications of PPPBP.

The procedure of Example 6 was also utilized to purify crude PPPBP containing 4.5% phenolphthalein (PP) and 950 ppm aminophenol (AP). The mother liquor (ML) of the first purification of PPPBP was reintroduced into the purification process to obtain subsequent batches of purified PPPBP. Table 6 shows that there is no change in purity of each batch of purified PPPBP for which recycled ML is used. In addition, the composition of the ML remained unchanged after four recycles (Table 7).

TABLE 6

Purification of PPPBP with recycled mother liquor

| | AP (%) | PP (%) | PPPBP purity (%) | Recovery (%) |
|---|---|---|---|---|
| PPPBP 1 | nd | 0.0288 | 99.9 | 90 |
| PPPBP 2 (1$^{st}$ recycle of ML) | 0.0011 | 0.0371 | 99.9 | 90 |
| PPPBP 3 (2$^{nd}$ recycle of ML) | 0.0007 | 0.0366 | 99.9 | 90 |
| PPPBP 4 (3$^{rd}$ recycle of ML) | 0.001 | 0.0423 | 99.9 | 89.5 |

TABLE 7

Mother liquor composition

| Recycle of ML | AP (%) | PP (%) | other impurities (%) | PPPBP purity (%) |
|---|---|---|---|---|
| ML 1 | nd | 11.06 | 0.58 | 88.37 |
| ML 2 | nd | 10.942 | 0.56 | 88.5 |

TABLE 7-continued

Mother liquor composition

| Recycle of ML | AP (%) | PP (%) | other impurities (%) | PPPBP purity (%) |
|---|---|---|---|---|
| ML 3 | nd | 11.455 | 0.54 | 88.1 |
| ML 4 | nd | 11.611 | 0.55 | 88.3 |

In addition, Table 8 shows the impurity profile of the purified PPPBP batches. Each impurity is represented by its retention time (via HPLC). As it is demonstrated here, there are no increases in impurities associated with recycling of the mother liquors.

TABLE 8

Impurity profile of purified PPPBP

| | HPLC Retention Time | | | |
|---|---|---|---|---|
| | 17.5 (%) | 17.8 (%) | 20.3 (%) | 21.6 (%) |
| PPPBP crude | 0.021 | 0.0113 | 0.0225 | 0.0398 |
| PPPBP 1 | 0.0145 | 0.00 | 0.0031 | 0.0036 |
| PPPBP 2 (1$^{st}$ recycle of ML) | 0.017 | 0.0007 | 0.0021 | 0.0064 |
| PPPBP 3 (2$^{nd}$ recycle of ML) | 0.0143 | 0.0009 | 0.0023 | 0.0055 |
| PPPBP 4 (3$^{rd}$ recycle of ML) | 0.0168 | 0.0008 | 0.002 | 0.0076 |
| PPPBP - using Example 7 procedure | 0.0223 | 0.007 | 0.0124 | 0.0211 |

In addition, the purification process of Example 6 was implemented for the purification of PPPBP produced by a method different from that of Example 1. Crude PPPBP was obtained from a procedure analogous to that of Example 1, but produced at a different production facility. As a result, the crude product contained a higher amount of AP (3394 ppm) and lower amount of PP (0.52%) than that observed for the procedure of Example 1. The results of the purification are shown in Table 9. AP and PP levels in the purified PPPBP were both at acceptably low levels after each recycling of the ML.

TABLE 9

Purification of PPPBP from alternative method

| | AP (%) | PP (%) |
|---|---|---|
| PPPBP 1 | nd | 0.0194 |
| PPPBP 2 (1$^{st}$ recycle of ML) | 0.001 | 0.0189 |
| PPPBP 3 (2$^{nd}$ recycle of ML) | 0.0014 | 0.021 |
| PPPBP 4 (3$^{rd}$ recycle of ML) | 0.0019 | 0.0225 |
| PPPBP 5 (20$^{th}$ recycle of ML) | 0.0014 | 0.0267 |

Additional alternative crude PPPBP obtained from a different production facility was also purified using the purification procedure of Example 6. The results of this purification are shown in Table 10.

TABLE 10

Purification of PPPBP from alternative method

| | AP (%) | PP (%) | PPPBP purity (%) |
|---|---|---|---|
| PPPBP 1 | nd | 0.017 | 99.9% |
| PPPBP 2 (1$^{st}$ recycle of ML) | 0.0016 | 0.0186 | 99.9% |
| PPPBP 3 (20$^{th}$ recycle of ML) | 0.0024 | 0.024 | 99.9% |

Example 11. Ion Exchange Resin Recycling

The procedure of Example 2 was utilized for purification of crude PPPBP (AP=1500±200 ppm; PP<1%; moisture ~26%). The spent ion exchange resin was subjected to a methanol wash prior to use in additional purifications of crude PPPBP. The process was repeated twice with spent ion exchange resin. Table 11 demonstrates that the re-used ion exchange resin provided similar impurity profiles along with high purity of PPPBP (entries 1-3).

The procedure of Example 2 was also utilized for purification of crude PPPBP (AP=2300±200 ppm; PP<1%; moisture ~26%). The spent ion exchange resin was subjected to a methanol wash prior to use in additional purifications of crude PPPBP. The process was repeated once with spent ion exchange resin. Table 11 demonstrates that the re-used ion exchange resin provided a similar impurity profile and similar high purity of recovered PPPBP (entries 4 and 5).

TABLE 11

Results of PPPBP purification with recycled ion exchange resin

|   | IER | Initial AP (ppm) | Final AP (ppm) | PP (ppm) | Unknown impurity (%) | PPPBP purity (%) |
|---|---|---|---|---|---|---|
| 1 | Fresh IER | 1500 | nd | 152 | 0.01 | >99.9 |
| 2 | 1st recycle | 1500 | nd | 170 | 0.01 | >99.9 |
| 3 | 2nd recycle | 1500 | 150 | 150 | 0.01 | >99.9 |
| 4 | Fresh IER | 2300 | nd | 117 | 0.01 | >99.9 |
| 5 | 1st recycle | 2300 | 80 | 135 | 0.01 | >99.85 |

IER = ion exchange resin;
AP = aminophenol;
PP = phenophthalein

Example 12. Ion Exchange Resin Regeneration

Into a 500 mL round bottom flask equipped with an overhead stirrer was added 100 g spent ion exchange resin (from 2 batches of PPPBP purification), methanol (700 mL), toluene (200 mL), and HCl (35%; 400 mL). The resulting mixture was allowed to stir for 3-4 h at rt. (Stirrer blade should be adjusted just below the surface of the solution in order to avoid breaking of IER beads.) The ion exchange resin was removed via filtration, and washed with 50 mL of a methanol/toluene mixture (38 mL methanol: 12 mL toluene) followed by 200 mL water (or until pH of washings are neutral). Methanol and toluene were recovered from filtrate by distillation. A final methanol wash (50 mL) was followed by drying of the ion exchange resin by suction. The mother liquor was recycled for the third cycle of IER regeneration. Methanol and toluene were recovered from the filtrate after the third recycle by distillation.

The regenerated ion exchange resin was then utilized in a purification of PPPBP using the purification procedure of Example 2. The results of this purification are shown below in Table 12.

TABLE 12

Purification of PPPBP with regenerated ion exchange resin

| | |
|---|---|
| Acidity of fresh IER (meq/g) | 4.8 ± 0.08 |
| Acidity of spent IER (meq/g) | 3.23 ± 0.07 |
| Acidity of regenerated IER (meq/g) | 4.54 ± 0.02 |
| Initial Aminophenol (ppm) | 2300 |
| Final Aminophenol (ppm) | 49 |
| Phenolphthalein (ppm) | 123 |
| Unknown impurity (%) | 0.08 |
| PPPBP purity (%) | 99.9 |

Optimization of the ion exchange resin regeneration procedure was investigated by the screening of a variety of solvents and conditions. Table 13 summarizes these conditions. These results show that the use of 3 volumes of an acetone/water mixture with 1 volume of HCl provided a 96% regeneration of the ion exchange resin while limiting the amount of solvent and acid required (entry 3). However, the methanol/toluene solvent system exemplified above in Example 12 and entries 4-7 is advantageous because it uses the same solvent mixture as the PPPBP purification process. By utilizing this solvent system and procedure, no cross-contamination from solvents such as acetone and water can occur in the purification process, and the IER regeneration is extremely efficient.

TABLE 13

Conditions screened for ion exchange resin regeneration

|   | Solvent | S-R | V-S | V-HCl | F-IER (meq/g) | S-IER (meq/g) | R-IER (meq/g) | R-% | Remarks |
|---|---|---|---|---|---|---|---|---|---|
| 1 | Methanol:Water | 4:1 | 10 | 3 | 4.8 | 3.6 | 4.1 | 85 | |
| 2 | Acetone:Water | 4:1 | 10 | 3 | 4.8 | 3.6 | 4.65 | 97 | |
| 3 | Acetone:Water | 4:1 | 3 | 1 | 4.8 | 3.6 | 4.6 | 96 | |
| 4 | Methanol:Toluene | 3.5:1 | 9 | 4 | 4.8 | 3.3 | 4.65 | 97 | Fresh solvent |
| 5 | Methanol:Toluene | — | — | — | 4.8 | 3.3 | 4.62 | 96.3 | ML of entry 4 |
| 6 | Methanol:Toluene | — | — | — | 4.8 | 3.3 | 4.6 | 96 | ML of entry 5 |
| 7 | Methanol:Toluene | — | — | 2 | 4.8 | 3.3 | 4.55 | 94.8 | ML of entry 6 and 2 volumes of HCl |

S-R = Solvent Ratio;
V-S = Volumes of Solvent;
V-HCl = Volumes of HCl;
F-IER = Acidiy of Fresh Ion Exchange Resin;
S-IER = Acidity of Spent Ion Exchange Resin;
R-IER = Acidity of Regenerated Ion Exchange Resin;
R-% = Regeneration Percent The optimized method of ion exchange resin regeneration (entry 4 of Table 13) was implemented and used in a series of purifications of PPPBP wherein the ion exchange resin was recycled and then regenerated after successive purifications. Table 14 demonstrates the results of these purifications. These results show that the overall purification process is efficient. The ion exchange resin can be recycled and used in a subsequent purification with no decrease in performance. Likewise, regeneration of the ion exchange resin is efficient and allows the resin to be reused and provide high yields of PPPBP with high purity. This process overall is very efficient due to the ability to recover and reuse solvents.

TABLE 14

PPPBP purification with regenerated ion exchange resin

| | IER | AP (%) | PP (%) | PPPBP purity (%) | Recovery (%) | Remarks |
|---|---|---|---|---|---|---|
| PPPBP 1 | Fresh | nd | 0.0152 | 99.9 | 92 | Fresh and |
| PPPBP 1A (1$^{st}$ recycle of IER) | recycled | nd | 0.017 | 99.9 | 92 | recycled IER |
| PPPBP 2 | regenerated | nd | 0.0179 | 99.9 | 92 | 1$^{st}$ |
| PPPBP 2A (recycle of IER) | recycled | 0.0029 | 0.021 | 99.9 | 92 | regenerated IER |
| PPPBP 3 | regenerated | 0.0033 | 0.0138 | 99.9 | 92 | 2$^{nd}$ |
| PPPBP 3A (recycle of IER) | recycled | 0.0034 | 0.014 | 99.9 | 92 | regenerated IER |
| PPPBP 4 | regenerated | 0.0040 | 0.0174 | 99.9 | 92 | 3$^{rd}$ |
| PPPBP 4A (recycle of IER) | recycled | 0.0045 | 0.0201 | 99.9 | 92 | regenerated IER |

Ion exchange resin regeneration (entry 3 of Table 13) was also implemented after purification of a batch of crude PPPBP produced from an alternative method and production facility. The initial purification of crude PPPBP (1% PP; AP=2000 ppm) was achieved using the procedure of Example 6 to provide PPPBP in 90% yield with purity and APHA meeting the required specifications. Urea was also measured to be less than 10 ppm by HPLC. The ion exchange resin was subsequently regenerated to provide the resin with 96% regeneration of acidity of the resin.

Example 13. Continuous PPPBP Purification

An apparatus for continuous purification of PPPBP was assembled. A feed tank containing crude PPPBP (20 g; 1% PP; 0.21% AP; moisture<1%) and urea (2 g) in methanol (340 mL; 17 volumes) was maintained at 50° C. Attached to the feed tank was a reactor containing the ion exchange resin (5 g; 2% cross-linked Rohm and Haas). Its temperature was also maintained at 50° C. The height of the reactor utilized was 3.0 inches and the diameter was 1.0 inch. The purification was accomplished using a WHSV (weight hourly space velocity=(lb of feed/hr)/(lb of catalyst)) of either 7 h$^{-1}$ or 10 h$^{-1}$. The results of these purifications are shown in Table 15. For these purifications, the adsorption efficiency of the ion exchange resin was measured to be 74%, which matches with results from the previous batch mod experiments. The ion exchange resin could be removed from the reactor and regenerated using the optimized method of Example 12 to provide the resin with an acidity of 4.6 meq/g (96% regeneration).

TABLE 15

Continuous PPPBP purification

| | WHSV = 10 h$^{-1}$ | | WHSV = 7 h$^{-1}$ | |
|---|---|---|---|---|
| Run time (h) | PPPBP quantity (g) | AP in effluent (ppm) | PPPBP quantity (g) | AP in effluent (ppm) |
| 1 | 3.1 | nd | 2.05 | Nd |
| 2 | 6.2 | 9 | 4.1 | Nd |
| 3 | 9.3 | 10 | 6.15 | Nd |
| 4 | 2.4 | 31 | 8.2 | 9 |

TABLE 15-continued

Continuous PPPBP purification

| | WHSV = 10 h$^{-1}$ | | WHSV = 7 h$^{-1}$ | |
|---|---|---|---|---|
| Run time (h) | PPPBP quantity (g) | AP in effluent (ppm) | PPPBP quantity (g) | AP in effluent (ppm) |
| 5 | 15.5 | 58 | 10.25 | 10 |
| 6 | — | — | 12.3 | 46 |

Further studies were done by varying the reactor height and diameter used in the continuous PPPBP purification experiments. These are summarized in Table 16. Both of the experiments of Table 16 incorporated a feed tank containing crude PPPBP (20 g; 1% PP; 0.21% AP; moisture<1%) and urea (2.5 g) in methanol (425 mL; 17 volumes). As in the previous experiment, the reactor contained ion exchange resin (5 g; 2% cross-linked Rohm and Haas) and the purification was accomplished using a WHSV of 10$^{-1}$. For these purifications, the adsorption efficiency of the ion exchange resin was measured to be 74-80%.

TABLE 16

Continuous PPPBP purification - varying reactor height/diameter

| | Height/diameter = 10/0.6 inch | | Height/diameter = 1.5/1.5 inch | |
|---|---|---|---|---|
| Run time (h) | PPPBP quantity (g) | AP in effluent (ppm) | PPPBP quantity (g) | AP in effluent (ppm) |
| 1 | 3.1 | nd | 2.05 | Nd |
| 2 | 6.2 | 9 | 4.1 | Nd |
| 3 | 9.3 | 10 | 6.15 | Nd |
| 4 | 2.4 | 31 | 8.2 | 9 |
| 5 | 15.5 | 58 | 10.25 | 10 |
| 6 | — | — | 12.3 | 46 |

Example 14. Optimization of the Volume of Methanol Required to Dissolve PPPBP Studies were undertaken to determine the amount of methanol required to bring PPPBP into solution at room temperature and at elevated temperature. Table 17 shows these results.

TABLE 17

Solubility of PPPBP in methanol

| Composition/temperature | Volumes of methanol |
| --- | --- |
| Pure PPPBP at room temp | 20 |
| 95% PPPBP + 5% PP at room temp | 17 |
| 92.5% PPPBP + 7.5% PP at room temp | 16 |
| 90% PPPBP + 10% PP at room temp | 15.5 |
| Pure PPPBP at reflux temp | 17 |
| 95% PPPBP + 5% PP at reflux temp | 13.5 |
| 92.5% PPPBP + 7.5% PP at reflux temp | 13 |
| 90% PPPBP + 10% PP at reflux temp | 13 |

Table 18 also shows the volume required of a methanol/water mixture to bring a crude mixture of 95% PPPBP and 5% PP into solution at reflux.

TABLE 18

Solubility of PPPBP in methanol/water

| 95% PPPBP + 5% PP | Volumes of methanol |
| --- | --- |
| Methanol:Water (9:1) at reflux temp | 14 |
| Methanol:Water (8:2) at reflux temp | 14 |
| Methanol:Water (7:3) at reflux temp | 16 |

Example 15. Exemplary Processes for Purification of PPPBP

Table 19 summarizes two exemplary processes disclosed.

TABLE 19

Exemplary processes

| Operation | Exemplary Process I | Exemplary Process II |
| --- | --- | --- |
| Crude wash | Cold Methanol | 9:1 Methanol:Water |
| Dissolution | 17 or 24 volumes methanol; 10% urea; 60° C. | 7 volumes Methanol/2 volumes toluene; 5% urea; 60° C. |
| Carbon treatment | 5% activated carbon (normal); 1 h | 5% activated carbon (normal); 1 h |
| Filtration | 60° C. | 60° C. |
| IER treatment | 50% w/w; 1 h; 60° C. | 50% w/w; 2 h; 60° C. |
| Filtration | 60° C. | 60° C. |
| Solvent distillation/Crystallization | Cool to 10° C. | 60% solvent distillation and cool to 10° C. |
| Filtration | 10° C. | 10° C. |
| Trituration | Only cold methanol wash (1 volume) | 95:5 methanol/water (2 volumes); 3 h; 60° C. |
| Water wash | 1 volume; 1 h; 100° C. | Only water wash |

For reasons of completeness, various aspects of the present disclosure are set out in the following numbered clauses:

Clause 1. A method of producing a purified 2-aryl-3,3-bis(4-hydroxyaryl)phthalimidine of formula (I) as disclosed herein, wherein $R^1$, at each occurrence, is selected from $C_1$-$C_{25}$ hydrocarbyl; $R_2$, at each occurrence, is selected from $C_1$-$C_{25}$ hydrocarbyl and halogen; p is 0, 1, 2, 3, 4, or 5; and q is 0, 1, 2, 3, or 4; the method comprising: (A) heating a reaction mixture comprising a phenolphthalein of formula (II) as disclosed herein, a primary aryl amine of formula (III) as disclosed herein, and an acid catalyst to form a phthalimidine of formula (I), wherein $R^1$, $R^2$, p, and q are as defined above; (B) precipitating the phthalimidine from the reaction mixture to provide a crude phthalimidine; (C) providing a solution comprising the crude phthalimidine, urea, and at least one solvent; (D) contacting the solution with one or more purification agents to provide a treated solution; (E) precipitating and recovering a phthalimidine adduct from the treated solution; and (F) recovering a purified compound of formula (I) from the adduct. Clause 2. The method of clause 1, wherein the compound of formula (I) is 2-phenyl-3,3-bis(4-hydroxyphenyl)phthalimidine ("PPPBP"). Clause 3. The method of clause 1 or clause 2, wherein the reaction mixture of (A) is heated to a temperature of 140° C. to 180° C., for a period of, for example, 20 hours to 50 hours. Clause 4. The method of any one of clauses 1-3, wherein the reaction mixture of (A) is heated to a temperature of 153° C. to 155° C. Clause 5. The method of any one of clauses 1-4, wherein the reaction mixture of (A) is heated to a temperature of 153° C. to 155° C. for a period of 22 hours. Clause 6. The method of any one of clauses 1-4, wherein the reaction mixture of (A) is heated to a temperature of 140° C. to 145° C. for a period of 45 hours. Clause 7. The method of any one of clauses 1-6, wherein (B) comprises quenching the reaction mixture of (A) by cooling the reaction mixture and adding an acid; filtering the precipitate; and washing the precipitate to provide the crude phthalimidine. Clause 8. The method of any one of clauses 1-7, wherein the crude phthalimidine comprises 1,000 ppm to 3,000 ppm, 1,200 ppm to 1,700 ppm, or 1,200 ppm to 1,500 ppm of an amino phenol impurity and 1 wt % to 2 wt % of residual phenolphthalein of formula (II). Clause 9. The method of any one of clauses 1-8, wherein the at least one solvent of (C) comprises an organic solvent. Clause 10. The method of any one of clauses 1-9, wherein the at least one solvent of (C) comprises an organic hydroxy compound, an organic ketone compound, an organic amide compound, an organic sulfoxide compound, an organic nitrile compound, an organic amine compound, an organic aromatic compound, or a combination thereof. Clause 11. The method of any one of clauses 1-10, wherein the at least one solvent of (C) comprises methanol, toluene, or a combination thereof. Clause 12. The method of any one of clauses 1-11, wherein the at least one solvent of (C) is methanol. Clause 13. The method of any one of clauses 1-11, wherein the at least one solvent of (C) comprises methanol and toluene in a ratio of 2-5:1 by volume. Clause 14. The method of any one of clauses 1-11, wherein the at least one solvent of (C) comprises methanol and toluene in a ratio of 3-4:1 by volume. Clause 15. The method of any one of clauses 1-11, wherein the at least one solvent of (C) comprises methanol and toluene in a ratio of 2-5:1 by volume, 3-4:1 by volume, or 3.5:1 by volume. Clause 16. The method of any one of clauses 1-15, wherein the volumes of the at least one solvent of (C) to the crude phthalimidine is 7-27:1 (e.g., 9:1, 17:1, or 24:1). Clause 17. The method of any one of clauses 1-16, wherein the urea is present in 5 wt % to 10 wt % based on wt % of the crude phthalimidine. Clause 18. The method of any one of clauses 1-17, wherein (D) comprises contacting the solution with activated carbon; contacting the solution with an ion exchange resin; or a combination thereof. Clause 19. The method of any one of clauses 1-18, wherein (D) comprises contacting the solution with the one or more purification agents to provide the treated solution; and filtering the treated solution to remove the one or more purification agents. Clause 20. The method of any one of clauses 1-19, wherein (D) comprises contacting the solution with activated carbon; removing the activated carbon by filtration; and treating the filtered solution with an ion exchange resin. Clause 21. The method of any one of clauses 1-20, wherein (D) comprises heating the solution at 55° C. to 60° C. when undergoing treatment with the one or more purification agents. Clause 22. The method of any one of clauses 1-21, wherein the one or more purification agents of (D) include a commercial grade activated carbon. Clause 23. The method of any one of clauses 1-22, wherein the one or more purification agents of (D) include an acidic ion exchange resin having an acid milliequivalents/gram of 4.8 to 5.0, and optionally 2% crosslinking Clause 24. The method of any one of clauses 1-23, wherein the loading of the one or more purification agents of (D) ranges from 5 wt % to 200 wt %, 10 wt % to 200 wt %, 5 wt % to 100 wt %, 5 wt % to 50 wt %, or 10 wt % to 50 wt %, based on wt % of the crude phthalimidine. Clause 25. The method of any one of clauses 1-24, wherein the one or more purification agents of (D) include a commercial grade activated carbon at 5 wt % based on wt % of the crude phthalimidine. Clause 26. The method of any one of clauses 1-25, wherein the one or more purification agents of (D) include an acidic ion exchange resin at 10 wt % to 200 wt % or 10 wt % to 50 wt % based on wt % of the crude phthalimidine. Clause 27. The method of any one of clauses 1-26, wherein the phthalimidine adduct of (E) is a phthalimidine-solvent adduct. Clause 28. The method of any one of clauses 1-27, wherein the phthalimidine adduct of (E) is a phthalimidine-methanol adduct. Clause 29. The method of any one of clauses 1-28, wherein (E) includes one or more of: filtering the treated solution to remove at least one of the one or more purification agents; distilling the treated solution, optionally under reduced pressure, to remove at least a portion of the at least one solvent; cooling the treated solution to precipitate the phthalimidine adduct; filtering the treated solution to recover the precipitated phthalimidine adduct; and triturating the phthalimidine adduct. Clause 30. The method of clause 29, wherein triturating the phthalimidine adduct comprises treating the precipitated phthalimidine adduct with a 95:5 methanol-water mixture. Clause 31. The method of any one of clauses 1-30, wherein precipitating the phthalimidine adduct of (E) is performed at 10° C. Clause 32. The method of any one of clauses 1-31, wherein (F) includes washing the phthalimidine adduct with hot water (e.g., washing the adduct over a filter, or re-slurrying the adduct and filtering; the wash water at 90° C. to 100 or 95° C. to 100° C.), followed by drying to provide the purified compound of formula (I). Clause 33. The method of clause 32, wherein the drying is performed at 100° C. to 110° C. Clause 34. The method of any one of clauses 1-33, wherein the yield of the purified compound of formula (I) is at least 80%. Clause 35. The method of any one of clauses 1-34, wherein the yield of the purified compound of formula (I) is at least 90% (e.g., 90%, 91%, 92%, 93%, or greater). Clause 36. The method of any one of clauses 1-35, where the volumes of the at least one solvent solvent:starting material is 7:1 to 27:1 or 7:1 to 9:1, and the yield of purified compound of formula (I) is at least 90% (e.g., at least 90%, at least 91%, at least 92%, at least 93%, or greater). Clause 37. The method of any one of clauses 1-36, wherein the purified compound of formula (I) comprises less than 50 ppm of amino phenol impurities and less than 500 ppm of residual phenolphthalein of formula (II). Clause 38. The method of any one of clauses 1-37, wherein one or more of the filtrates generated in (B) through (F) are recycled through one or more of steps (B) through (F) to recover additional purified compound of formula (I). Clause 39. The method of any one of clauses 1-38, wherein the filtrate ("mother liquor") generated in (E) after precipitating and recovering the phthalimidine adduct is recycled through steps (E) and (F) to recover additional purified compound of formula (I) (e.g., the yield for a first crop may be 92%; the yield for a second crop based on recovery from filtrates (e.g., mother liquor) can be 2-3%, providing a total yield of 94-95%). Clause 40. The method of any one of clauses 1-39, wherein one or more of the filtrates generated in (A) through (F) are subjected to distillation to recover one or more the solvents. Clause 41. The method of clause 40, wherein solvent recovery is 90%. Clause 42. The method of any one of clauses 1-41, wherein at least one of the one or more purification agents used in the method is recycled and used again in the method of any one of clauses 1-41. Clause 43. The method of any one of clauses 1-42, wherein at least one of the one or more purification agents is recycled at least one time and used again in the method of any one of clauses 1-41, wherein the purity of the compound of formula (I) recovered using the recycled purification agent is greater than or equal to 99.80%, greater than or equal to 99.85%, or greater than or equal to 99.90%. Clause 44. The method of any one of clauses 1-43, wherein at least one of the one or more purification agents is recycled at least two times and used again in the method of any one of clauses 1-41, wherein the purity of the compound of formula (I) recovered using the recycled purification agent is greater than or equal to 99.80%, greater than or equal to 99.85%, or greater than or equal to 99.90%. Clause 45. The method of any one of clauses 1-44, wherein at least one of the one or more purification agents is recycled at least one time and used again in the method of any one of clauses 1-41, and the amount of aminophenol impurity in the purified compound of formula (I) is 10% or less of the initial amount in the crude phthalimidine. Clause 46. The method of any one of clauses 1-45, wherein at least one of the one or more purification agents is recycled at least two times and used again in the method of any one of clauses 1-41, and the amount of aminophenol impurity in the purified compound of formula (I) is 10% or less of the initial amount in the crude phthalimidine. Clause 47. The method of any one of clauses 41-46, wherein the recycled purification agent is an ion exchange resin. Clause 48. The method of any one of clauses 1-47, wherein at least one of the one or more purification agents used in the method is regenerated. Clause 49. The method of clause 48, wherein the purification agent is regenerated and used at least one time in the method of any one of clauses 1-47 and the purity of the compound of formula (I) recovered is greater than or equal to 99.80%, greater than or equal to 99.85%, or greater than or equal to 99.90%. Clause 50. The method of clause 48, wherein the purification agent is regenerated and used at least one time in the method of any one of clauses 1-47 and the amount of aminophenol impurity in the purified compound of formula (I) is 3% or less of the initial amount in the crude phthalimidine. Clause 51. The method of any of clauses 1-50, wherein at least one of the one or more purification agents used in the method is regenerated by a process comprising (a) treatment of the spent purification agent with acid in one or more solvents; (b) filtration of the resultant regenerated purification agent; and (c) washing of the regenerated purification agent with one or more solvents (e.g., with an organic solvent followed by an aqueous solvent). Clause 52. The method of clause 51, wherein the acid of step (a) is concentrated hydrochloric acid, the one or more solvents of step (a) is toluene, methanol, or a combination thereof, and the one or more solvents of step (c) is toluene, methanol, water, or a combination thereof. Clause 53. The method of clause 52, wherein the ratio of methanol:toluene in step (a) is 3.5:1. Clause 54. The method of clause 53, wherein the volumes of methanol-toluene in step (a) is 9 volumes relative to the purification agent, and the volume of hydrochloric acid is 4 volumes relative to the purification agent. Clause 55. The method of any one of clauses 51-54, wherein the acidity of the purification agent is regenerated to at least 90% or at least 95% of its original acidity, as measured by milliequivalents of hydronium ion per gram of resin. Clause 56. The method of any one of clauses 51-55, wherein the purification agent is an ion exchange resin. Clause 57. The method of any one of clauses 51-56, wherein at least a portion of the one or more solvents used in (a)-(c) are recovered. Clause 58. The method of any one of clauses 51-57, wherein at least 90% of the methanol, toluene, or a combination thereof used in the regeneration process is recovered. Clause 59. The method of clause 51, wherein the acid of step (a) is concentrated hydrochloric acid, the solvents of step (a) are acetone and water, and the one or more solvents of step (c) is acetone, water, or a combination thereof. Clause 60. The method of clause 59, wherein the ratio of acetone:water in step (a) is 4:1. Clause 61. The method of clause 60, wherein the combined volume of acetone and water in step (a) is 3 volumes relative to the purification agent, and the volume of hydrochloric acid is 1 volume relative to the purification agent. Clause 62. The method of any of clauses 59-61, wherein the acidity of the purification agent is regenerated to at least 90% or at least 95% of its original acidity, as measured by milliequivalents of hydronium ion per gram of resin. Clause 63. The method of any one of clauses 59-62, wherein the purification agent is an ion exchange resin. Clause 64. The method of any one of clauses 59-63, wherein at least a portion of the one or more solvents of (a)-(c) are recovered. Clause 65. The method of clause 64, wherein at least 85% of acetone used in the regeneration process is recovered. Clause 66. The method of any one of clauses 1-65, wherein the cycle time for the process of (A)-(F) is 40 hours. Clause 67. The method of any one of clauses 1-66 comprising a continuous process, the continuous process comprising one or more of: subjecting one or more of the filtrates generated in (A) through (F) to distillation to recover one or more the solvents, and reusing the distilled solvents; recycling at least one of the one or more purification agents used in the method and reusing the recycled purification agent; and regenerating at least one of the one or more purification agents used in the reusing the regenerated purification agent. Clause 68. A method of producing a purified 2-aryl-3,3-bis(4-hydroxyaryl)phthalimidine of formula (I) as disclosed herein, wherein $R^1$, at each occurrence, is selected from $C_1$-$C_{25}$ hydrocarbyl; $R_2$, at each occurrence, is selected from $C_1$-$C_{25}$ hydrocarbyl and halogen; p is 0, 1, 2, 3, 4, or 5; and q is 0, 1, 2, 3, or 4; the method comprising: (A) heating a reaction mixture comprising a phenolphthalein of formula (II) as disclosed herein, a primary aryl amine of formula (III) as disclosed herein, and an acid catalyst to form a phthalimidine of formula (I), wherein $R^1$, $R^2$, p, and q are as defined above; (B) precipitating the phthalimidine from the reaction mixture to provide a crude phthalimidine; (C) providing a solution comprising the crude phthalimidine and methanol; (D) precipitating and recovering a phthalimidine adduct from the treated solution; and (F) recovering a purified compound of formula (I) from the adduct; wherein the method does not include use of activated carbon. Clause 69. A copolymer comprising repeating units derived from the purified compound of formula (I) according to any one of clauses 1-68. Clause 70. The compolymer of clause 69, comprising further comprising repeating units derived from bisphenol-A.

What is claimed is:

1. A method of producing a purified 2-aryl-3,3-bis(4-hydroxyaryl)phthalimidine of formula (I),

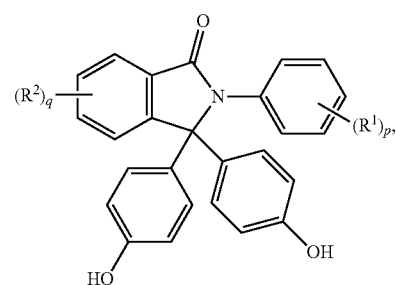

wherein $R^1$, at each occurrence, is selected from $C_1$-$C_{25}$ hydrocarbyl; $R_2$, at each occurrence, is selected from $C_1$-$C_{25}$ hydrocarbyl and halogen; p is 0, 1, 2, 3, 4, or 5; and q is 0, 1, 2, 3, or 4; the method comprising:

(A) heating a reaction mixture comprising a phenolphthalein of formula (II), a primary aryl amine of formula (III), and an acid catalyst to form a phthalimidine of formula (I),

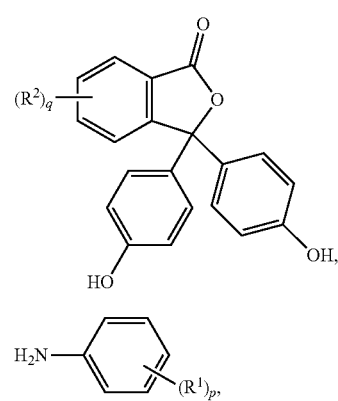

wherein $R^1$, $R^2$, p, and q are as defined above;

(B) precipitating the phthalimidine from the reaction mixture to provide a crude phthalimidine;

(C) providing a solution comprising the crude phthalimidine, urea, and at least one solvent;

(D) contacting the solution with one or more purification agents to provide a treated solution;

(E) precipitating and recovering a phthalimidine adduct from the treated solution; and (F) recovering a purified compound of formula (I) from the adduct.

2. The method of claim 1, wherein the compound of formula (I) is 2-phenyl-3,3-bis(4-hydroxyphenyl)phthalimidine ("PPPBP").

3. The method of claim 1, wherein the reaction mixture of (A) is heated to a temperature of 140° C. to 180° C.

4. The method of claim 1, wherein (B) comprises quenching the reaction mixture of (A) by cooling the reaction mixture and adding an acid; filtering the precipitate; and washing the precipitate to provide the crude phthalimidine.

5. The method of claim 1, wherein (D) comprises contacting the solution with activated carbon; contacting the solution with an ion exchange resin; or a combination thereof.

6. The method of claim 1, wherein (D) comprises contacting the solution with the one or more purification agents to provide the treated solution; and filtering the treated solution to remove the one or more purification agents.

7. The method of claim 1, wherein the phthalimidine adduct of (E) is a phthalimidine-solvent adduct.

8. The method of claim 1, wherein (E) includes one or more of:

filtering the treated solution to remove at least one of the one or more purification agents;

distilling the treated solution, optionally under reduced pressure, to remove at least a portion of the at least one solvent;

cooling the treated solution to precipitate the phthalimidine adduct;

filtering the treated solution to recover the precipitated phthalimidine adduct; and triturating the phthalimidine adduct.

9. The method of claim 1, wherein precipitating the phthalimidine adduct of (E) is performed at 10° C.

10. The method of claim 1, wherein (F) includes washing the phthalimidine adduct with hot water, followed by drying to provide the purified compound of formula (I).

11. The method of claim 1, wherein the yield of the purified compound of formula (I) is at least 80%.

12. The method of claim 1, where the volumes of the at least one solvent solvent:starting material is 7:1 to 9:1, and the yield of purified compound of formula (I) is at least 90%.

13. The method of claim 1, wherein the purified compound of formula (I) comprises less than 50 ppm of amino phenol impurities and less than 500 ppm of residual phenolphthalein of formula (II).

14. The method of claim 1, wherein at least one of the one or more purification agents is recycled at least two times and used again in the method of any one of claims 1-13, wherein the purity of the compound of formula (I) recovered using the recycled purification agent is greater than or equal to 99.85%.

15. The method of claim 1, wherein at least one of the one or more purification agents used in the method is regenerated.

16. The method of claim 1, wherein the cycle time for the process of (A)-(F) is 40 hours.

17. The method of claim 1 comprising a continuous process, the continuous process comprising one or more of:

subjecting one or more of the filtrates generated in (A) through (F) to distillation to recover one or more the solvents, and reusing the distilled solvents;

recycling at least one of the one or more purification agents used in the method and reusing the recycled purification agent; and regenerating at least one of the one or more purification agents used in the reusing the regenerated purification agent.

18. The method of claim 1, wherein the method does not include use of activated carbon.

19. A copolymer comprising repeating units derived from the purified compound of formula (I) according to claim 1.

20. The copolymer of claim 19, comprising further comprising repeating units derived from bisphenol-A.

* * * * *